United States Patent [19]
Jacobson et al.

[11] Patent Number: 5,470,984
[45] Date of Patent: Nov. 28, 1995

[54] 1-DIMETHYLCARBAMOYL-3-SUBSTITUTED-5-SUBSTITUTED-1H-1,2,4-TRIAZOLES

[75] Inventors: Richard M. Jacobson, Chalfont; J. Roger Ramsay, Quakertown; Harold E. Aller, Norristown; Muthuvelu Thirugnanam, Langhorne, all of Pa.

[73] Assignee: Shell Research Limited, United Kingdom

[21] Appl. No.: 240,362

[22] Filed: May 10, 1994

Related U.S. Application Data

[62] Division of Ser. No. 601,496, Oct. 22, 1990, Pat. No. 5,319,092, which is a continuation of Ser. No. 878,759, Jul. 2, 1986, abandoned, which is a continuation-in-part of Ser. No. 759,016, Jul. 25, 1985, Pat. No. 4,742,072.

[51] Int. Cl.$^6$ .................. C07D 249/12; A01N 43/653
[52] U.S. Cl. .................. 548/264.4; 544/112; 546/210
[58] Field of Search .................. 548/264.4; 514/384, 514/236.2, 326; 544/112; 546/210

[56] References Cited

U.S. PATENT DOCUMENTS

| | | | |
|---|---|---|---|
| 3,973,028 | 8/1976 | Doyle, Jr. et al. | 424/269 |
| 4,742,072 | 5/1988 | Jacobson et al. | 514/384 |
| 4,970,224 | 11/1990 | Jacobson et al. | 514/384 |
| 5,015,652 | 5/1991 | Jacobson et al. | 514/384 |
| 5,319,092 | 6/1994 | Jacobson et al. | 548/264.4 |

*Primary Examiner*—José G. Dees
*Assistant Examiner*—Barbara S. Frazier

[57] ABSTRACT

This invention relates to 1-dimethylcarbamoyl-3-substituted-5-substituted-1H-1,2,4-triazoles as defined herein, compositions containing those compounds and methods of use.

76 Claims, No Drawings

1-DIMETHYLCARBAMOYL-3-SUBSTITUTED-5-SUBSTITUTED-1H-1,2,4-TRIAZOLES

This is a divisional of application Ser. No. 07/601,496 filed on Oct. 22, 1990, now U.S. Pat. No. 5,319,092 which is a CONT of Ser. No. 06/878,759filed Jul. 2, 1986, which is a CIP of Ser. No. 06/759,016filed Jul. 25, 1985, now U.S. Pat. No. 4,742,072.

BACKGROUND OF THE INVENTION

This invention relates to novel 1-dimethylcarbamoyl-3-substituted-5-substituted-1H-1,2,4-triazoles which are useful as insecticides, acaricides, molluscicides and/or plant growth regulating agents, compositions containing those compounds and methods of use.

The search for compounds which have a combination of excellent activity and low undesirable toxicity is a continuing one because of factors such as the desire for compounds exhibiting greater activity, better selectivity, low undesirable environmental impact, low production cost and effectiveness against insects resistant to many known insecticides.

Certain compounds of the present invention, as defined herein, are particularly suitable for controlling plant-destructive insects from the order Homoptera in agriculture and horticulture. Certain compounds of the present invention, as defined herein, control foliage feeding insects in other orders such as Coleoptera, Lepidoptera and/or acarids as shown by the biological evaluation data herein. Certain compounds of the present invention as more fully defined herein are particuarly suitable for use in regulating plant growth. Further, certain compounds of the present invention as more fully defined herein are particularly suitable for controlling molluscs.

Certain 1,2,4-triazoles have been disclosed as having pesticidal activity. U.S. Pat. No. 3,308,131 describes a group of 1,2,4-triazoles having the general formula

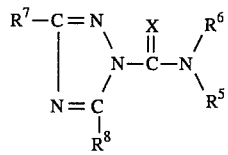

and

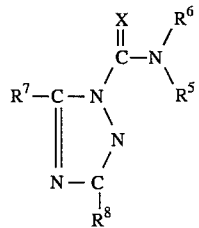

where X is oxygen or sulfur, $R^5$ and $R^6$ are aliphatic groups containing up to 14 carbons and which may be joined to form a heterocyclic ring with the carbamoyl nitrogen atom and $R^7$ and $R^8$ which together contain up to 14 carbon atoms, are free from aliphatic unsaturation and are selected from hydrogen, halogen, sulfonyl, mercapto, cyano, hydrocarbyl, halohydrocarbyl, nitrohydrocarbyl, hydroxycarbyloxycarbonylhydrocarbyl, hydrocarbylsulfonyl, hydrocarbylmercapto, nitrohydrocarbylmercapto, halohydrocarbylmercapto, aminohydrocarbylmercapto and hydrocarbyloxyhydrocarbyl. These compounds are said to be useful as insecticides, in dyeing textiles and as analgesics.

U.S. Pat. No. 4,291,043 describes 1-N,N-dimethyl-carbamoyl- 3(5)-alkyl-5(3 )-alkylthioalkylthio-1,2,4-triazoles having insecticidal activity. The 3(5) substituents include i-propyl, s-butyl, t-butyl or optionally methyl-substituted cyclopropyl and a group having the formula

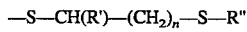

where R' is H or methyl, R" is lower $(C_1-C_4)$alkyl and n is zero or 1.

U.S. Pat. No. 3,973,028 describes 1-dimethyl-carbamoyl-3-branched alkyl-1,2,4-triazol-5-yl-(N-substituted)sulfonamides having insecticidal activity.

U.S. Pat. No. 4,054,664 describes 1(2)-(N,N-disubstituted carbamoyl)-3,5-substituted-1,2,4-triazoles having insecticidal activity. The 3(5) substituents include isopropyl, s-butyl, t-butyl, and S—R where R is methyl, ethyl, propyl, vinyl, prop-2-ynyl, but-2-enyl or 2-haloalkyl.

U.S. Pat. No. 4,160,839 discloses 1-N,N-dimethylcarbamoyl- 3,5-substituted-1,2,4-triazoles having insecticidal activity. The 3-substituents include t-butyl, propyl, cyclopropyl, isopropyl or 1-methylpropyl. The 5-substituents include S—R where R is 2-propynyl, allyl, 2-bromoallyl, 2-chloroallyl, 2-methylallyl, 1-methylallyl or 2,3,3-trichloroallyl.

U.S. Pat. No. 4,220,790 discloses 1-N,N-dimethyl-carbamoyl- 3-tert-butyl-5-methylthio-1,2,4-triazole having insecticidal activity.

European Patent Application 0029407 discloses 1-N,N-dimethylcarbamoyl- 3(5) -alkyl-5(3) -alkoxyalkylthio-1,2,4-triazoles where the 3(5)-substituent is isopropyl, sec-butyl, t-butyl, or cyclopropyl optionally substituted by methyl; and the 5(3)-substituent is $S(CH_2)_nOR^2$ where $R^2$ is $(C_1-C_3)$alkyl and n is 1 or 2.

The present invention discloses 1-dimethylcarbamoyl-3-substituted-5-substituted-1H-1,2,4-triazoles. These compounds are distinguished primarily by their novel 5-position substituents.

The 5-position acid and ester compounds of the present invention are distinguished by their excellent insecticidal activity against sucking insects of the order Homoptera and especially those of the family Aphididae. These acid and ester compounds are highly selective against aphids, possess very good contact action and are plant systemic through both foliar and root absorption; and exhibit very good residual properties as foliar deposits and through both foliar and root absorption and transport.

Certain compounds of the present invention, generally the 5-position carbonyl, amido, sulfonyl and sulfonamide compounds, exhibit a broader spectrum of activity against foliage feeding insects, such as those from the order Coleoptera, and Acarids, in addition to exhibiting activity against insects from the order Homoptera.

Certain compounds of the present invention are also distinguished by their plant growth regulator effect. Further, certain compounds of the present invention are distinguished by their molluscicidal activity.

Accordingly, compounds of the present invention are particularly suitable for controlling plant-destructive insects and/or acarids in crops of cultivated plants and ornamentals, especially in crops of fruits, vegetables and cereals. Certain compounds are suitable as plant growth regulating agents and certain compounds are suitable for controlling molluscs.

It is therefore an object of the present invention to provide novel compounds and compositions containing said compounds which possess selective aphpicidal activity. It is also an object of the present invention to provide novel compounds, and compositions containing said compounds which possess insecticidal and acaricidal activity. It is a further object of this invention to provide methods for controlling insects, acarids, regulating plant growth and/or controlling molluscs using the novel compounds.

SUMMARY OF THE INVENTION

In accordance with the present invention, there are provided compounds having the formula:

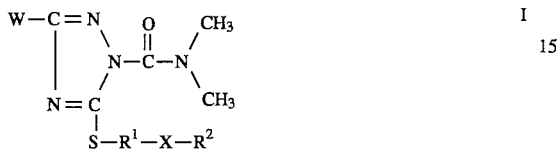

wherein
R$^1$ is an unsubstituted or substituted (C$_1$–C$_6$) straight chain alkylidene (—(CH$_2$)$_n$—) group having one to four of the same or different substituents selected from cyano; nitro; OR; CO$_2$R; OCOR; COR; lower (C$_2$–C$_6$)alkenyl; lower (C$_2$–C$_6$)alkynyl; lower (C$_1$–C$_6$)alkyl; or unsubstituted or substituted phenyl having one to three of the same or different halo, cyano, nitro, trifluoromethoxy, difluoromethoxy, tetrafluoroethoxy, trifluorothiomethoxy, tetrafluorothiomethoxy, CO$_2$R, COR, OCOR, lower (C$_1$–C$_4$)-alkyl, lower (C$_1$–C$_4$)alkoxy, lower (C$_1$–C$_4$)haloalkyl or lower (C$_2$–C$_6$)alkenyl;

X is

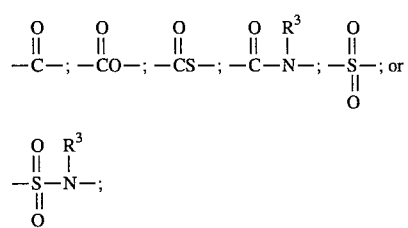

R$^2$ is hydrogen; unsubstituted or substituted (C$_1$–C$_6$)alkyl where the substituent is halo, cyano, nitro, OR, CO$_2$R, COR, or OCOR;
unsubstituted or substituted phen(C$_1$–C$_4$)alkyl where the phenyl ring has one to three of the same or different substituents selected from halo, cyano, nitro, trifluoromethoxy, difluoromethoxy, tetrafluoroethoxy, trifluorothiomethoxy, tetrafluorothiomethoxy, CO$_2$R, COR, OCOR, lower(C$_1$–C$_4$)alkyl, lower (C$_1$–C$_4$)alkoxy, lower (C$_1$–C$_4$)haloalkyl or lower (C$_2$–C$_6$)alkenyl;
unsubstituted or substituted phenyl having one to three of the same or different substituents selected from halo, cyano, nitro, trifluoromethoxy, difluoromethoxy, tetrafluoroethoxy, trifluorothiomethoxy, tetrafluorothioethoxy, CO$_2$R, COR, OCOR, lower (C$_1$–C$_4$)alkyl, lower (C$_1$–C$_4$)alkoxy, lower (C$_1$–C$_4$)haloalkyl or lower (C$_2$–C$_6$)alkenyl;
R$^3$ is hydrogen; or (C$_1$–C$_6$)alkyl;
R$^2$ and R$^3$ can be taken together along with the nitrogen atom to which they are attached to form a pyrrolidino, morpholino or piperidino ring; is isopropyl; sec-butyl; t-butyl; t-amyl; or 2-methylthio-2-propyl;
where R is hydrogen; lower (C$_1$–C$_6$)alkyl; or phenyl optionally substituted with one to three of the same or different halo, cyano, nitro, hydroxy, trifluoromethyl, trifluoromethoxy, difluoromethoxy, tetrafluoroethoxy, trifluorothiomethoxy, tetrafluorothioethoxy, lower (C$_1$–C$_4$)alkyl, lower (C$_1$–C$_4$)alkoxy, lower (C$_1$–C$_4$)haloalkyl, lower (C$_2$–C$_6$)alkenyl, carboxy, lower (C$_1$–C$_4$)alkoxycarbonyl; and
agronomically acceptable salts thereof.

Further, in accordance with the present invention, there are provided compositions containing compounds of the present invention and methods of using said compounds and compositions.

DETAILED DESCRIPTION OF THE INVENTION

The term "halo" includes chloro, fluoro, bromo and iodo. The term "alkyl" by itself or as a part of another substituent should be understood as including straight or branched chain groups such as methyl, ethyl, n-propyl, isopropyl, n-butyl, t-butyl, isobutyl, neopentyl and the like. The term "haloalkyl" is an alkyl group of the stated number of carbon atoms having one or more of the same or different halo atoms bonded thereto such as bromomethyl, dichloromethyl, trifluoromethyl, fluorochloromethyl, tetrafluoroethyl and the like. It will be recognized by those skilled in the art that when X is SO$_2$ and R$^2$ is hydrogen, tautomeric rearrangement to S(O)OH is anticipated.

Typical compounds within the scope of the present invention include, but are not limited to:
1-dimethylcarbamoyl-3-(2-methylthio-2-propyl)-5-(1-(N-(3-cyano-2,6-dichlorophenyl)-carboxamido)-but-3-ynylthio)-1H-1,2,4-triazole
1-dimethylcarbamoyl-3-(2-methylthio-2-propyl)-5-(1-(morpholinocarbonyl)-propylthio)-1H-1,2,4-triazole
1-dimethylcarbamoyl-3-(2-methylthio-2-propyl)-5-(1-(pyrrolidinocarbonyl)-ethylthio)-1H-1,2,4-triazole
1-dimethylcarbamoyl-3-(2-methylthio-2-propyl)-5-(2-(piperidinocarbonyl)-ethylthio)-1H-1,2,4-triazole
1-dimethylcarbamoyl-3-(2-methylthio-2-propyl)-5-(3-carboethoxybutylthio)-1H-1,2,4-triazole
1-dimethylcarbamoyl-3-(2-methylthio-2-propyl)-5-(3-carboethoxypropylthio)-1H-1,2,4-triazole
1-dimethylcarbamoyl-3-(2-methylthio-2-propyl)-5-(N-(3-nitrobenzyl)-carboxamidomethylthio)-1H-1,2,4-triazole
1-dimethylcarbamoyl-3-(2-methylthio-2-propyl)-5-(N-(4-methylbenzyl)-carboxamidomethylthio)-1H-1,2,4-triazole
1-dimethylcarbamoyl-3-(2-methylthio-2-propyl)-5-(N-benzylcarboxamidomethylthio)-1H-1,2,4-triazole
1-dimethylcarbamoyl-3-(2-methylthio-2-propyl)-5-(N-carbomethoxymethyl-N-phenylcarboxamidomethylthio)-1H-1,2,4-triazole
1-dimethylcarbamoyl-3-(2-methylthio-2-propyl)-5-(N-ethyl-N-phenyl carboxamido methylthio)-1H-1,2,4-triazole
1-dimethylcarbamoyl-3-(2-methylthio-2-propyl)-5-(N-methyl-N-phenylcarboxamidomethylthio)-1H-1,2,4-triazole
1-dimethylcarbamoyl-3-(2-methylthio-2-propyl)-5-(N-phenethylcarboxamidomethylthio)-1H-1,2,4-triazole
1-dimethylcarbamoyl-3-(2-methylthio-2-propyl)-5-(N-phenylcarboxamidomethylthio)-1H-1,2,4-triazole
1-dimethylcarbamoyl-3-(2-methylthio-2-propyl)-5-(carboethoxymethylthio)-1H-1,2,4-triazole 1-dimethylcarbamoyl-3-(2-methylthio-2-propyl)-5-(morpholinocarbonylmethylthio)- 1H-1,2,4-triazole
1-dimethylcarbamoyl-3-(2-methylthio-2-propyl)-5-(piperidinocarbonylmethylthio)- 1H-1,2,4-triazole
1-dimethylcarbamoyl-3-(2-methylthio-2-propyl)-5-(pyrrolidinocarbonylmethylthio)- 1H-1,2,4-triazole
1-dimethylcarbamoyl-3-i-propyl-5-((2-chlorophenyl)-sulfonylethylthio)- 1H-1,2,4-triazole
1-dimethylcarbamoyl-3-i-propyl-5-(1-carboethoxybutylthio)-1H-1,2,4-triazole
1-dimethylcarbamoyl-3-i-propyl-5-(1-carboethoxyethylthio)-1H-1,2,4-triazole
1-dimethylcarbamoyl-3-i-propyl-5-(1-carboxamido-1-propionylmethylthio)- 1H-1,2,4-triazole
1-dimethylcarbamoyl-3-i-propyl-5-(2-(N,N-dimethylcarboxamido)- 1-(3-trifluoromethoxy-4-chlorophenyl)-ethylthio)- 1H-1,2,4-triazole
1-dimethylcarbamoyl-3-i-propyl-5-(2-N, N-diethylcarboxamido- 4-methoxybutylthio)-1H-1,2,4-triazole
1-dimethylcarbamoyl-3-i-propyl-5-(N,N-bis-(2-acetoxypropyl)-carboxamidomethylthio)- 1H-1,2,4-triazole
1-dimethylcarbamoyl-3-i-propyl-5-(N,N-bis-(2-methoxyethyl)-carboxamidomethylthio)- 1H-1,2,4-triazole
1-dimethylcarbamoyl-3-i-propyl-5-(N,N-diethylcarboxamidomethylthio)- 1H-1,2,4-triazole
1-dimethylcarbamoyl-3-i-propyl-5-(N,N-dimethylcarboxamidomethylthio)- 1H-1,2,4-triazole
1-dimethylcarbamoyl-3-i-propyl-5-(N-(2-carbomethoxyphenyl)-sulfonamidomethylthio)- 1H-1,2,4-triazole
1-dimethylcarbamoyl-3-i-propyl-5-(N-(2-chloroethyl)carboxamidomethylthio)- 1H-1,2,4-triazole
1-dimethylcarbamoyl-3-i-propyl-5-(N-methylcarboxamidomethylthio)- 1H-1,2,4-triazole
1-dimethylcarbamoyl-3-i-propyl-5-(acetylmethylthio)-1H-1,2,4-triazole
1-dimethylcarbamoyl-3-i-propyl-5-(carboethoxymethylthio)-1H-1,2,4-triazole
1-dimethylcarbamoyl-3-i-propyl-5-(carboxamidomethylthio)-1H-1,2,4-triazole
1-dimethylcarbamoyl-3-i-propyl-5-(phenylsulfonylmethylthio)- 1H-1,2,4-triazole
1-dimethylcarbamoyl-3-s-butyl-5-(1-(N,N-dimethylcarboxamido)- 1-cyanoethylthio)-1H-1,2,4-triazole
1-dimethylcarbamoyl-3-s-butyl-5-(1-(N,N-dimethylcarboxamido)-ethylthio)- 1H-1,2,4-triazole
1-dimethylcarbamoyl-3-s-butyl-5-(1-(N-(2-nitroethyl)carboxamido)-ethylthio)- 1H-1,2,4-triazole
1-dimethylcarbamoyl-3-s-butyl-5-(1-(N-(3-ketobutyl)carboxamidoethylthio)- 1H-1,2,4-triazole
1-dimethylcarbamoyl-3-s-butyl-5-(1-carboethoxy-2-acetoxyethylthio)- 1H-1,2,4-triazole
1-dimethylcarbamoyl-3-s-butyl-5-(1-carbomethoxyethylthio)-1H-1,2,4-triazole
1-dimethylcarbamoyl-3-s-butyl-5-(1-carbomethoxypentylthio)- 1H-1,2,4-triazole
1-dimethylcarbamoyl-3-s-butyl-5-(1-carboxamidoethylthio)-1H-1,2,4-triazole
1-dimethylcarbamoyl-3-s-butyl-5-(1-carboxamidopentylthio)-1H-1,2,4-triazole
1-dimethylcarbamoyl-3-s-butyl-5-(1-carboxybut-3-enylthio)-1H-1,2,4-triazole
1-dimethylcarbamoyl-3-s-butyl-5-(2-((ethylthio)-carbonyl)ethylthio-1H-1,2,4-triazole
1-dimethylcarbamoyl-3-s-butyl-5-(2-(N,N-dimethylcarboxamido)-ethylthio)-1H-1,2,4-triazole
1-dimethylcarbamoyl-3-s-butyl-5-(2-(N,N-dipropylcarboxamido)-ethylthio)- 1H-1,2,4-triazole
1-dimethylcarbamoyl-3-s-butyl-5-(2-carboethoxy-2-phenylethylthio)- 1H-1,2,4-triazole
1-dimethylcarbamoyl-3-s-butyl-5-(2-carboethoxyethylthio)- 1H-1,2,4-triazole
1-dimethylcarbamoyl-3-s-butyl-5-(2-carboxamidobutylthio)- 1H-1,2,4-triazole
1-dimethylcarbamoyl-3-s-butyl-5-(2-carboxamidoethylthio)- 1H-1,2,4-triazole
1-dimethylcarbamoyl-3-s-butyl-5-(3-carboisopropoxy-1-cyanopropylthio)- 1H-1,2,4-triazole
1-dimethylcarbamoyl-3-s-butyl-5-(4-carbomethoxybutylthio)- 1H-1,2,4-triazole
1-dimethylcarbamoyl-3-s-butyl-5-(4-carbomethoxyphenylacetylmethylthio)- 1H-1,2,4-triazole
1-dimethylcarbamoyl-3-s-butyl-5-(acetoxymethylsulfonylethylthio)- 1H-1,2,4-triazole
1-dimethylcarbamoyl-3-s-butyl-5-(bis-(carbopropoxy)methylthio)- 1H-1,2,4-triazole
1-dimethylcarbamoyl-3-s-butyl-5-(carbo-(2-chloroethoxy)ethylthio)- 1H-1,2,4-triazole
1-dimethylcarbamoyl-3-s-butyl-5-(carboethoxyethylthio)-1H -1,2,4-triazole
1-dimethylcarbamoyl-3-s-butyl-5-(carboethoxymethylthio)- 1H-1,2,4-triazole
1-dimethylcarbamoyl-3-s-butyl-5-(carboisopropoxymethylthio)- 1H-1,2,4-triazole
1-dimethylcarbamoyl-3-s-butyl-5-(carbomethoxymethylthio)- 1H-1,2,4-triazole
1-dimethylcarbamoyl-3-s-butyl-5-(carbopropoxymethylthio)- 1H-1,2,4-triazole
1-dimethylcarbamoyl-3-s-butyl-5-(carboxymethylthio)-1H-1,2,4-triazole
1-dimethylcarbamoyl-3-s-butyl-5-(ethylsulfonylmethylthio)- 1H-1,2,4-triazole
1-dimethylcarbamoyl-3-s-butyl-5-(methylsulfonylmethylthio)- 1H-1,2,4-triazole
1-dimethylcarbamoyl-3-t-amyl-5-(1,2-bis-(carbo-i-butoxy)ethylthio)- 1H-1,2,4-triazole
1-dimethylcarbamoyl-3-t-amyl-5-(1,2-bis-(carboethoxy)ethylthio)- 1H-1,2,4-triazole
1-dimethylcarbamoyl-3-t-amyl-5-(1,2-bis-(carbomethoxy)propylthio)- 1H-1,2,4-triazole
1-dimethylcarbamoyl-3-t-amyl-5-(1-(N-ethyl-N-methylcarboxamido)- 1-(2-fluoro-4-nitrophenyl)-methylthio)-1H-1,2,4-triazole
1-dimethylcarbamoyl-3-t-amyl-5-(1-carbo-(2-cyanoethoxy)prop- 2-yl-thio)-1H-1,2,4-triazole
1-dimethylcarbamoyl-3-t-amyl-5-(1-carboethoxyprop-2-yl-thio)- 1H-1,2,4-triazole
1-dimethylcarbamoyl-3-t-amyl-5-(1-carboxy-3-nitropropylthio)- 1H-1,2,4-triazole
1-dimethylcarbamoyl-3-t-amyl-5-(1-carboxyethylthio)-1H-1,2,4-triazole
1-dimethylcarbamoyl-3-t-amyl-5-(1-carboxyethylthio)-1H-1,2,4-triazole potassium salt
1-dimethylcarbamoyl-3-t-amyl-5-(2-(N-ethylcarboxamido)- 1-(4-tetrafluorothioethoxyphenyl)-ethylthio)-1H-1,2,4 -triazole
1-dimethylcarbamoyl-3-t-amyl-5-(2-carbobutoxypropylthio)- 1H-1,2,4-triazole
1-dimethylcarbamoyl-3-t-amyl-5-(2-carbomethoxypropylthio)- 1H-1,2,4-triazole
1-dimethylcarbamoyl-3-t-amyl-5-(2-carboxybutylthio)-1H-1,2,4-triazole
1-dimethylcarbamoyl-3-t-amyl-5-(2-carboxyethylthio)-1H-1,2,4-triazole
1-dimethylcarbamoyl-3-t-amyl-5-(5-carboethoxypentylthio)-1H-1,2,4-triazole 1-dimethylcarbamoyl-3-t-amyl-5-(6-carbo-t-butoxyhexylthio)- 1H-1,2,4-triazole
1-dimethylcarbamoyl-3-t-amyl-5-(N-ethyl-N-methylcarboxamidomethylthio)- 1H-1,2,4-triazole
1-dimethylcarbamoyl-3-t-amyl-5-(N-ethylcarboxamidomethylthio)- 1H-1,2,4-triazole
1-dimethylcarbamoyl-3-t-amyl-5-(carbo-t-butoxymethylthio)- 1H-1,2,4-triazole
1-dimethylcarbamoyl-3-t-amyl-5-(carboethoxymethylthio)-1H- 1,2,4-triazole
1-dimethylcarbamoyl-3-t-amyl-5-(carboxyhexylthio)-1H-1,2,4-triazole dimethylammonium salt
1-dimethylcarbamoyl-3-t-amyl-5-(carboxymethylthio)-1H-1,2,4-triazole sodium salt
1-dimethylcarbamoyl-3-t-amyl-5-(carboxymethylthio)-1H-1,2,4-triazole tetraethylammonium salt
1-dimethylcarbamoyl-3-t-amyl-5-(formylmethylthio)-1H-1,2,4-triazole
1-dimethylcarbamoyl-3-t-butyl-5-(1,2-bis-(carboethoxy)ethylthio)- 1H-1,2,4-triazole
1-dimethylcarbamoyl-3-t-butyl-5-(1-(N,N-dimethylcarboxamido)-ethylthio)- 1H-1,2,4-triazole
1-dimethylcarbamoyl-3-t-butyl-5-(1-carboethoxyethylthio)-1H-1,2,4-triazole
1-dimethylcarbamoyl-3-t-butyl-5-(1-carboethoxyprop-2-ylthio)- 1H-1,2,4-triazole
1-dimethylcarbamoyl-3-t-butyl-5-(1-carbomethoxy-1-phenylmethylthio)- 1H-1,2,4-triazole
1-dimethylcarbamoyl-3-t-butyl-5-(1-carbomethoxyethylthio)- 1H-1,2,4-triazole
1-dimethylcarbamoyl-3-t-butyl-5-(1-carboxamidoethylthio)- 1H-1,2,4-triazole
1-dimethylcarbamoyl-3-t-butyl-5-(1-carboxyethylthio)-1H-1,2,4-triazole
1-dimethylcarbamoyl-3-t-butyl-5-(2-((methylthio)carbonyl)-methylthio)- 1H-1,2,4-triazole
1-dimethylcarbamoyl-3-t-butyl-5-(2-(N,N-dimethylcarboxamido)-ethylthio)- 1H-1,2,4-triazole
1-dimethylcarbamoyl-3-t-butyl-5-(2-carboethoxyethylthio)-1H-1,2,4-triazole
1-dimethylcarbamoyl-3-t-butyl-5-(2-carbomethoxypropylthio)- 1H-1,2,4-triazole
1-dimethylcarbamoyl-3-t-butyl-5-(2-carboxamidoethylthio)- 1H-1,2,4-triazole
1-dimethylcarbamoyl-3-t-butyl-5-(2-carboxyethylthio)-1H-1,2,4-triazole
1-dimethylcarbamoyl-3-t-butyl-5-(3-carboethoxypropylthio)-1H-1,2,4-triazole
1-dimethylcarbamoyl-3-t-butyl-5-(N,N-diethylcarboxamidomethylthio)- 1H-1,2,4-triazole
1-dimethylcarbamoyl-3-t-butyl-5-(N,N-dimethylcarboxamidomethylthio)- 1H-1,2,4-triazole
1-dimethylcarbamoyl-3-t-butyl-5-(N, N-dimethylsulfonamidomethylthio)- 1H-1,2,4-triazole
1-dimethylcarbamoyl-3-t-butyl-5-(N-benzylcarboxamidomethylthio)- 1H-1,2,4-triazole
1-dimethylcarbamoyl-3-t-butyl-5-(N-ethyl-N-methylcarboxamidomethylthio)- 1H-1,2,4-triazole
1-dimethylcarbamoyl-3-t-butyl-5-(N-ethylcarboxamidomethylthio)- 1H-1,2,4-triazole
1-dimethylcarbameyl-3-t-butyl-5-(N-methyl-N-phenylcarboxamidomethylthio)- 1H-1,2,4-triazole
1-dimethylcarbamoyl-3-t-butyl-5-(N-methylcarboxamidomethylthio)-1H-1,2,4-triazole
1-dimethylcarbamoyl-3-t-butyl-5-(N-phenylcarboxamidomethylthio)- 1H-1,2,4-triazole
1-dimethylcarbamoyl-3-t-butyl-5-(acetylethylthio)-1H-1,2,4-triazole
1-dimethylcarbamoyl-3-t-butyl-5-(acetylmethylthio)-1H-1,2,4-triazole
1-dimethylcarbamoyl-3-t-butyl-5-(bis-(carboethoxy)methylthio)- 1H-1,2,4-triazole
1-dimethylcarbamoyl-3-t-butyl-5-(carbo-t-butoxymethylthio)- 1H-1,2,4-triazole
1-dimethylcarbamoyl-3-t-butyl-5-(carboethoxyethylthio)-1H-1,2,4-triazole
1-dimethylcarbamoyl-3-t-butyl-5-(carboethoxymethylthio)-1H-1,2,4-triazole
1-dimethylcarbamoyl-3-t-butyl-5-(carboisopropoxymethylthio)- 1H-1,2,4-triazole
1-dimethylcarbamoyl-3-t-butyl-5-(carbomethoxymethylthio)-1H-1,2,4-triazole
1-dimethylcarbamoyl-3-t-butyl-5-(carbopropoxymethylthio)-1H-1,2,4-triazole
1-dimethylcarbamoyl-3-t-butyl-5-(carboxamidomethylthio)-1H-1,2,4-triazole
1-dimethylcarbamoyl-3-t-butyl-5-(carboxymethylthio)-1H-1,2,4-triazole
1-dimethylcarbamoyl-3-t-butyl-5-(carboxymethylthio)-1H1,2,4-triazole sodium salt
1-dimethylcarbamoyl-3-t-butyl-5-(formylmethylthio)-1H-1,2,4-triazole
1-dimethylcarbamoyl-3-t-butyl-5-(formylpropylthio)-1H-1,2,4-triazole
1-dimethylcarbamoyl-3-t-butyl-5-(methylsulfonylmethylthio)- 1H-1,2,4-triazole
1-dimethylcarbamoyl-3-t-butyl-5-(morpholinocarbonylmethylthio)- 1H-1,2,4-triazole
1-dimethylcarbamoyl-3-t-butyl-5-(phenylsulfonylmethylthio)- 1H-1,2,4-triazole
1-dimethylcarbamoyl-3-t-butyl-5-(piperidinocarbonylmethylthio)- 1H-1,2,4-triazole
1-dimethylcarbamoyl-3-t-butyl-5-(pyrrolidinocarbonylmethylthio)- 1H-1,2,4-triazole
1-dimethylcarbamoyl-3-t-butyl-5-(trimethylacetylethylthio)- 1H-1,2,4-triazole Those compounds of the present invention useful for selectively controlling insects from the order Homoptera, and most particularly, those from the family Aphididae, in the presence of other insects and acarids (herein at time referred to as "selective aphicides") are those of Formula I where $R^1$, W and R are as defined above for Formula I and, independently X is $-CO_2-$;
$R^2$ is hydrogen or lower $(C_1-C_6)$alkyl;
and agronomically acceptable salts thereof.

Because of their activity, compounds preferred as selective aphicides are those of Formula I where $R^1$ is unsubstituted or substituted $(C_1-C_6)$ alkylidene group having one or two substituents selected from cyano, $CO_2R$, lower $(C_1-C_6)$alkyl or phenyl;

X is $-CO_2-$;

R and $R^2$ are independently, hydrogen or lower $(C_1-C_6)$ alkyl;

W is t-butyl or isopropyl; and
agronomically acceptable salts thereof.

Compounds of the present invention most preferred as selective aphicides are those of Formula I where $R^1$ is $-CH_2-$, $-CH_2CH_2-$, $-CH_2-CH_2CH_2-$, or $-CH(CH_3)-$;

X is $-CO_2-$;

$R^2$ is hydrogen or lower $(C_1-C_4)$alkyl;

W is t-butyl; and agronomically acceptable salts thereof.

Those compounds of the present invention which in addition to exhibiting aphicidal activity are useful as broader spectrum insecticides and acaricides are those of Formula I wherein X is

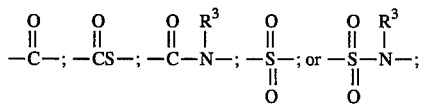

and agronomically acceptable salts thereof; where R, $R^1$, $R^2$, $R^3$ and W are as defined above for Formula I.

Because of their activity, those compounds of Formula I preferred as broad spectrum insecticides and acaricides are those where $R^1$ is an unsubstituted or substituted $(C_1-C_4)$alkylidene group having one or two
substituents selected from lower $(C_1-C_4)$alkyl;

X is

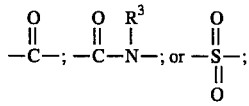

$R^2$ is hydrogen, lower $(C_1-C_4)$alkyl, phenyl or benzyl;
$R^3$ is hydrogen or lower $(C_1-C_4)$alkyl;
$R^2$ and $R^3$ can be taken together along with the nitrogen atom to which they are attached to form a pyrrolidino, morpholino or piperidino ring;
W is t-butyl;
and agronomically acceptable salts thereof.

Compounds of the present invention most preferred as broad spectrum insecticides and acaricides are those of Formula I where $R^1$ is —$CH_2$—; —$CH_2CH_2$—; or

X is

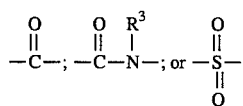

$R^2$ is hydrogen, methyl, ethyl, t-butyl, phenyl or benzyl;
$R^3$ is hydrogen, methyl or ethyl;
$R^2$ and $R^3$ can be taken together along with the nitrogen atom to which they are attached to form a pyrrolidino, morpholino or piperidino ring;
W is t-butyl; and
agronomically acceptable salts thereof.

Compounds of Formula I useful as plant growth regulators are those where $R^1$ is —$CH_2$—;
X is —$CO_2$—;
$R^2$ is hydrogen or $(C_1-C_3)$ straight chain alkyl;

W is t-butyl; and
agronomically acceptable salts thereof; preferably where $R^2$ is ethyl.

Compounds of Formula I useful as molluscicides are those where $R^1$ is —$CH_2$— or —$CH(CH_3)$—;
X is —$CO_2$—;

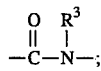

or —$SO_2$—;
$R^2$ is hydrogen, methyl or ethyl;
$R^3$ is hydrogen or lower $(C_1-C_4)$alkyl;
W is t-butyl; t-amyl; or 2-methylthio-2-propyl;
and agronomically acceptable salts thereof.

Compounds of Formula I preferred as molluscicides are those where $R^1$ is —$CH_2$—;
X is —$CO_2$— or

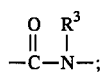

$R^2$ and $R^3$ are, independently, hydrogen, methyl or ethyl
W is t-butyl; and agronomically acceptable salts thereof.

Since the 1-dimethylcarbamoyl-3-substituted-5-substituted-1H-1,2,4-triazoles of Formula I may possess acidic or basic functional groups, they may form novel salts with appropriate bases or acids which also exhibit insecticidal, plant growth regulatory and/or molluscicidal activity. Typical salts are the agronomically acceptable metal salts, ammonium salts and acid addition salts. Among the metal salts are those in which the metal cation is an alkali metal cation such as sodium, potassium, lithium or the like; alkaline earth metal cation such as calcium, magnesium, barium, strontium or the like; or heavy metal cation such as zinc, manganese, cupric, cuprous, ferric, ferrous, titanium, aluminum or the like. Among the ammonium salts are those in which the ammonium cation has the formula $NR^4R^5R^6R^7$ wherein each of $R^4$, $R^5$, $R^6$ and $R^7$ are independently a hydrogen atom, a hydroxy group, a $(C_1-C_4)$alkoxy group, a $(C_1-C_{20})$alkyl group, a $(C_3-C_8)$ alkenyl group, a $(C_3-C_8)$ alkynyl group, a $(C_2-C_8)$hydroxyalkyl group, a $(C_2-C_8)$alkoxyalkyl group, a $(C_2-C_6)$aminoalkyl group, a $(C_2-C_6)$haloalkyl group, an amino group, a $(C_1-C_4)$alkyl or $(C_1-C_4)$dialkylamino group, a substituted or unsubstituted phenyl group, a substituted or unsubstituted phenylalkyl group, having up to four carbon atoms in the alkyl moiety, or any two of $R^4$, $R^5$, $R^6$ or $R^7$ can be taken together to form with the nitrogen atom a 5- or 6-membered heterocyclic ring, optionally having up to one additional hetero atom (e.g., oxygen, nitrogen, or sulfur) in the ring, and preferably saturated, such as piperidino, morpholino, pyrrolidino, piperazino or the like, or any three of $R^4$, $R^5$, $R^6$ or $R^7$ can be taken together to form with the nitrogen atom a 5-or 6-membered aromatic heterocyclic ring, such as pyrazine or pyridine. When the ammonium group contains a substituted phenyl or substituted phenylalkyl group, the substituents will generally be selected from halogen atoms, $(C_1-C_8)$alkyl groups, $(C_1-C_4)$alkoxy groups, hydroxy group, nitro groups, trifluoromethyl groups, cyano groups, amino groups, $(C_1-C_4)$alkylthio groups, and the like. Such substituted phenyl groups preferably have up to two such substituents. Representative ammonium cations include ammonium, dimethylammonium, 2-ethylhexylammonium, bis(2-hydroxyethyl)ammonium, tris (2-hydroxyethyl) ammonium, dicyclohexylammonium, t-octylammonium, 2-hydroxyethylammonium, morpholinium, piperidinium, 2-phenethylammonium, 2-methylbenzylammonium, n-hexylammonium, triethylammonium, trimethylammonium, tri(n-butyl)-ammonium, methoxyethylammonium, diisopropylammonium, pyridinium, dialkylammonium, pyrazolium, propargylammonium, dimethylhydrazinium, octadecylammonium, 4-dichlorophenylammonium, 4-nitrobenzylammonium, benzyltrimethylammonium, 2-hydroxyethyldimethyloctadecylammonium, 2-hydroxyethyldiethyloctylammonium, decyltrimethylammonium, hexyltriethylammonium, 4-methylbenzyltrimethylammonium, and the like. Among the acid addition salts are those in which the anion is an agronomically acceptable anion such as chloride, bromide, sulfate, nitrate, perchlorate, acetate, oxalate and the like.

The 1-dimethylcarbamoyl-3-substituted-5-substituted-1H-1,2,4-triazoles of the present invention or their precursors are prepared by S-alkylating a 3-substituted-5-thio-1H-1,2,4-triazole in the presence of a solvent or mixture of solvents which is inert to the reactants and optionally an acid scavenger with a compound having the formula

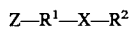

Z—R¹—X—R²   II where $R^1$, X and $R^2$ are as defined above for Formula I and Z is a good leaving group such as halo (chloro, bromo or iodo), alkyl sulfonates such as methane sulfonate, or phenyl or substituted phenyl sulfonates such as paratoluene sulfonate to obtain 3-substituted-5-substituted- 1H-1,2,4-triazoles.

Suitable solvents for the above process include methanol, ethanol, tetrahydrofuran, dimethylformamide, or acetonitrile.

Suitable acid scavengers for the above process, such as triethylamine or diisopropylethylamine my be added during alkylation or, if desired, the 3-substituted-5-thio- 1H-1,2,4-triazole could be pretreated with an acid scavenger such as sodium hydride, sodium hydroxide, potassium hydroxide or the like.

Modifications to the above process my be necessary to accommodate reactive functionalities of particular 5-substituents. Such modifications would be apparent and known to those skilled in the art.

The 3-substituted-5-substituted-1H-1,2,4-triazole obtained by the above process is then reacted with a compound having the formula

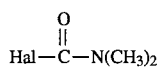

$$\overset{O}{\underset{\|}{Hal-C-N(CH_3)_2}}$$   III where Hal is halogen (chloro, bromo or iodo) in the presence of a suitable acid scavenger and optionally a suitable acylation catalyst.

Suitable acid scavengers for this process include tertiary amines such as triethylamine and pyridine.

Suitable acylation catalysts include 4-dimethylaminopyridine.

The compounds of Formula II are commercially available, such as ethyl bromoacetate, or can be prepared from commercially available materials by procedures known to those skilled in the art.

The 3-substituted-5-thio-1H-1,2,4-triazoles used as a starting material can be prepared from known precursors by known methods as illustrated below for Example No. 2, part (a).

Preparation of the compounds of the present invention is carried out at temperatures between about −70° C. and about 150° C. Preferably, the reactions are carried out between about 0° C. and about 100° C.

Although higher or lower pressures can be used if desired, preparation of the compounds of the present invention is preferably carried out at about atmospheric pressure.

Substantially equimolar amounts of reactants are preferably used, although higher or lower amounts can be used if desired.

Modifications to the above process may be necessary to accommodate reactive functionalities of particular substituents. Such modifications would be apparent to and known by those skilled in the art.

The agronomically acceptable salts embraced by Formula I of the invention can be prepared by reacting a metal hydroxide, a metal hydride or an amine or ammonium salt, such as a halide, hydroxide or alkoxide with a compound of Formula I having one or more carboxy groups or reacting a quaternary ammonium salt, such as chloride, bromide, nitrate or the like with a metal salt of a compound of Formula I in a suitable solvent. When metal hydroxides are used as reagents, useful solvents include water; ethers such as glyme, dioxane, tetrahydrofuran and the like; alcohols such as methanol, ethanol, isopropanol and the like. When metal hydrides are used as reagents, useful solvents include nonhydroxylic solvents, for example, ethers such as dioxane, glyme, tetrahydrofuran, diethyl ether and the like; hydrocarbons such as toluene, xylene, hexane, pentane, heptane, octane, and the like; dimethylformamide, and the like. When amines are used as reagents, useful solvents include alcohols, such as methanol or ethanol; hydrocarbons, such as toluene, xylene, hexane and the like; tetrahydrofuran; glyme; dioxane; or water. When ammonium salts are used as reagents, useful solvents include water; alcohols, such as methanol or ethanol; glyme; tetrahydrofuran; or the like. When the ammonium salt is other than a hydroxide or alkoxide, an additional base, such as potassium or sodium hydroxide, hydride, or alkoxide is generally used. The particular choice of solvent will depend on the relative solubilities of the starting materials and the resultant salts, and slurries rather than solutions of certain reagents may be used to obtain the salts. Generally, equivalent amounts of the starting reagents are used and the salt-forming reaction is carried out between about 0° C. to about 100° C., preferably at about room temperature.

The acid addition salts of the present invention can be prepared by reacting hydrochloric, hydrobromic, sulfuric, nitric, phosphoric, acetic, propionic, benzoic or other suitable acid with a compound of the present invention having a basic functional group in a suitable solvent such as water, alcohols, ethers, esters, ketones, haloalkanes and the like. The particular choice of solvent will depend on the relative solubilities of the starting materials and the resulting salts and slurries rather than solutions of certain reagents may be used to obtain the salts. Generally, equivalent molar amounts of starting materials are used and the salt-forming reaction is carried out between about −10° C. to about 100° C., preferably at about room temperature.

The following examples will further illustrate this invention but are not intended to limit it in any way. In Table I, some 1-dimethylcarbamoyl-3-substituted-5-substituted-1H-1,2,4-triazoles of the present invention that have been made are listed. The structures of these compounds were confirmed by NMR and in some cases by IR and/or elemental analysis. Specific illustrative preparation of the compounds of Examples 2, 4, 6, 7, 10, 20, 24, 25, 30, 32, 34, 35 and 40 are described after Table I.

TABLE I $$W-C=N\underset{N=C}{\overset{|}{\underset{|}{\vphantom{X}}}}N-\overset{O}{\overset{\|}{C}}-N\overset{CH_3}{\underset{CH_3}{\diagdown\diagup}}$$
$$\phantom{W-C=N}S-R^1-X-R^2$$

| Ex. No. | W | $R^1$ | X | $R^2$ | m.p. °C. |
|---|---|---|---|---|---|
| 1 | $-C(CH_3)_3$ | $-CH_2-$ | $-CO_2-$ | $CH_3$ | Solid |
| 2 | $-C(CH_3)_3$ | $-CH_2-$ | $-CO_2-$ | $-CH_2CH_3$ | 55 |
| 3 | $-C(CH_3)_3$ | $-CH_2-$ | $-CO_2-$ | $-C(CH_3)_3$ | Oil |
| 4 | $-C(CH_3)_3$ | $-CH(CH_3)-$ | $-CO_2-$ | $-CH_2CH_3$ | Oil |
| 5 | $-C(CH_3)_3$ | $-CH(CH_3)-$ | $-CO_2-$ | $CH_3$ | Oil |
| 6 | $-C(CH_3)_3$ | $-CH_2CH_2CH_2-$ | $-CO_2-$ | $-CH_2CH_3$ | Oil |
| 7 | $-C(CH_3)_3$ | $-CH_2CH_2-$ | $-CO_2-$ | $CH_3$ | Oil |
| 8 | $-C(CH_3)_3$ | $-CH_2-$ | $-CO_2-$ | $-CH_2CH_2CH_3$ | Oil |
| 9 | $-C(CH_3)_3$ | $-CH_2-$ | $-CO_2-$ | $-CH(CH_3)_2$ | Oil |
| 10 | $-C(CH_3)_3$ | $-CH_2-$ | $-CO_2-$ | H | Oil |
| 11 | $-C(CH_3)_3$ | $-CH_2CH_2-$ | $-CO_2-$ | $-CH_2CH_3$ | Oil |
| 12 | $-C(CH_3)_3$ | $-CH_2-$ | $-CO_2-$ | Na | 178–180 |
| 13 | $-C(CH_3)_3$ | $-C(CH_3)_2-$ | $-CO_2-$ | $-CH_2CH_3$ | 50–51 |
| 14 | $-C(CH_3)_3$ | $-CH(CO_2CH_2CH_3)CH_2-$ | $-CO_2-$ | $-CH_2CH_3$ | Oil |
| 15 | $-C(CH_3)_3$ | $-CH(CH_3)-$ | $-CO_2-$ | H | 85–91 |
| 16 | $-C(CH_3)_3$ | $-CH_2CH_2-$ | $-CO_2-$ | H | Oil |
| 17 | $-C(CH_3)_3$ | $-CH_2-$ | $-\overset{O}{\overset{\|}{C}}-\overset{CH_3}{\underset{\|}{N}}-$ | $CH_3$ | 82–84 |
| 18 | $-C(CH_3)_3$ | $-CH_2-$ | $-\overset{O}{\overset{\|}{C}}-\overset{H}{\underset{\|}{N}}-$ | H | 165–166 |
| 19 | $-C(CH_3)_3$ | $-CH_2-$ | $-\overset{O}{\overset{\|}{C}}-\overset{CH_2CH_3}{\underset{\|}{N}}-$ | $-CH_2CH_3$ | Oil |
| 20 | $-C(CH_3)_3$ | $-CH_2-$ | $-\overset{O}{\overset{\|}{C}}-\overset{H}{\underset{\|}{N}}-$ | $CH_3$ | 87–88 |
| 21 | $-C(CH_3)_3$ | $-CH_2-$ | $-\overset{O}{\overset{\|}{\underset{\|}{S}}}-\underset{O}{\vphantom{X}}$ | $C_6H_5$ | 115–116 |
| 22 | $-C(CH_3)_3$ | $-CH_2-$ | $-\overset{O}{\overset{\|}{C}}-\overset{H}{\underset{\|}{N}}-$ | $C_6H_5$ | 122–123 |
| 23 | $-C(CH_3)_3$ | $-CH_2-$ | $-\overset{O}{\overset{\|}{C}}-\overset{H}{\underset{\|}{N}}-$ | $-CH_2C_6H_5$ | Oil |
| 24 | $-C(CH_3)_3$ | $-CH_2-$ | $-\overset{O}{\overset{\|}{C}}-\overset{CH_3}{\underset{\|}{N}}-$ | $-C_6H_5$ | 119–120 |
| 25 | $-C(CH_3)_3$ | $-CH_2-$ | $-\overset{O}{\overset{\|}{\underset{\|}{S}}}-\underset{O}{\vphantom{X}}$ | $CH_3$ | 109–110 |
| 26 | $-C(CH_3)_3$ | $-CH_2CH_2-$ | $-\overset{O}{\overset{\|}{C}}-\overset{H}{\underset{\|}{N}}-$ | H | 131–132 |
| 27 | $-C(CH_3)_3$ | $-CH_2CH_2-$ | $-\overset{O}{\overset{\|}{C}}-\overset{CH_3}{\underset{\|}{N}}-$ | $CH_3$ | Oil |
| 28 | $-C(CH_3)_3$ | $-CH(CH_3)-$ | $-\overset{O}{\overset{\|}{C}}-\overset{H}{\underset{\|}{N}}-$ | H | 160–162 |

TABLE I-continued $$\begin{array}{c} W-C=N \\ | \\ N=C \\ | \\ S-R^1-X-R^2 \end{array} \quad N-\overset{O}{\underset{\|}{C}}-N\overset{CH_3}{\underset{CH_3}{\diagup}}$$

| Ex. No. | W | R¹ | X | R² | m.p. °C. |
|---|---|---|---|---|---|
| 29 | —C(CH₃)₃ | —CH(CH₃)— | $\overset{O}{\underset{\|}{-C}}-\overset{CH_3}{\underset{\|}{N}}-$ | CH₃ | Oil |
| 30 | —C(CH₃)₃ | —CH₂— | $\overset{O}{\underset{\|}{-C}}-\overset{CH_3}{\underset{\|}{N}}-$ | CH₂CH₃ | Oil |
| 31 | —C(CH₃)₃ | —CH₂— | $\overset{O}{\underset{\|}{-C}}-\overset{H}{\underset{\|}{N}}-$ | —CH₂CH₃ | 113–114 |
| 32 | —C(CH₃)₃ | —CH₂CH(CH₃)— | —CO₂— | —CH₃ | Oil |
| 33 | —CH₂C(CH₃)₃ | —CH₂— | —CO₂— | —CH₂CH₃ | Oil |
| 34 | —C(CH₃)₂CH₂CH₃ | —CH₂— | —CO₂— | —CH₂CH₃ | Oil |
| 35 | —C(CH₃)₂SCH₃ | —CH₂— | —CO₂— | —CH₂CH₃— | Oil |
| 36 | —C(CH₃)₃ | —CH₂— | $\overset{O}{\underset{\|}{-C-}}$ | —C(CH₃)₃ | 102–103 |
| 37 | —C(CH₃)₃ | —CH₂— | $\overset{O}{\underset{\|}{-C-}}$ | H | Oil |
| 38 | —C(CH₃)₃ | —CH₂— | $\overset{O}{\underset{\|}{-C-}}$ | CH₃ | Oil |
| 39 | —C(CH₃)₃ | —CH₂— | —CO₂— | —CH₂CH₃ | Oil |
| 40 | —C(CH₃)₃ | —CH₂— | $\overset{O}{\underset{\underset{O}{\|}}{-S-}}\overset{CH_3}{\underset{\|}{N}}-$ | —CH₃ | 83–85 |
| 41 | —C(CH₃)₃ | —CH₂— | $\overset{O}{\underset{\|}{-C-}}$ | —N⟨pyrrolidinyl⟩ | 132–133 |
| 42 | —C(CH₃)₃ | —CH₂— | $\overset{O}{\underset{\|}{-C-}}$ | —N⟨piperidinyl⟩ | Oil |
| 43 | —C(CH₃)₃ | —CH₂— | $\overset{O}{\underset{\|}{-C-}}$ | —N⟨morpholinyl⟩ | Oil |
| 44 | —C(CH₃)₃ | —CH(CO₂CH₂CH₃)— | —CO₂— | —CH₂CH₃ | Oil |
| 45 | —C(CH₃)₃ | —CH(4-Cl-C₆H₄)— | —CO₂— | CH₃ | Oil |

EXAMPLE NO. 2

Preparation of 1-dimethylcarbamoyl-3-t-butyl-5-carboethoxymethylthio- 1H-1,2,4-triazole Method 1:
(a) Preparation of 3-t-butyl-5-thio-1H-1,2,4-triazole Into a 5 liter 4 necked flask equipped with a mechanical stirrer, reflux condenser, thermometer, and addition funnel was added 500 g (5.5 mole) of thiosemicarbazide, 1000 ml of 1,4-dioxane, and a solution of 220 g (5.5 mole) of sodium hydroxide in 920 ml of water. The mixture was stirred and cooled with an external bath to maintain the temperature at near 25° C. while 630 ml (5.1 mole) of trimethylacetyl chloride was added over the course of 30 minutes. After stirring an additional 30 minutes, the precipitated trimethylacetylthiosemicarbazide was collected by filtration and used as is in the next reaction.

All of the wet trimethylacetylthiosemicarbazide was suspended in a solution of 450 g (11.25 mole) of sodium hydroxide in 1900 ml of water and the suspension was heated to 90° C. until all was in solution and then the reaction mixture was heated an additional 1 hour. After cooling the mixture was acidified with concentrated hydrochloric acid and let stand overnight. The resulting crystals were collected by filtration and washed with water and ethyl ether to yield 320 g (2.1 mole) of 3-t-butyl- 5-thio-1H-1,2,4-triazole. m.p. 205° C.

(b) Preparation of 3-t-butyl-5-carboethoxymethylthio-1H-1,2,4-triazole

To 157 g (1.0 mole) of 3-t-butyl-5-thio-1H-1,2,4-triazole in 500 ml of ethanol was added 110 ml (0.99 mole) of ethyl bromoacetate. The resulting mixture was refluxed for two hours, cooled, concentrated under vacuum, and partitioned between ether and aqueous ammonium hydroxide. The organic layer was washed with brine, dried over magnesium sulfate, and concentrated under vacuum yielding 143 g (0.59 mole) 3-t-butyl-5-carboethoxymethylthio-1H-1,2,4-triazole. m.p. 93° C.

(c) Preparation of 1-dimethylcarbamoyl-3-t-butyl-5-carboethoxymethylthio- 1H-1,2,4-triazole To 100 g (0.411 mole) of 3-t-butyl-5-carboethoxy-methylthio- 1H-1,2,4-triazole, 6 g (0.05 mole) of 4-dimethylaminopyridine, and 200 ml of pyridine was added 54 g (0.50 mole) of dimethylcarbamoyl chloride. The resulting solution was refluxed for eight hours and allowed to cool overnight. The reaction mixture was concentrated under vacuum, partitioned between ether and dilute hydrochloric acid. The organic layer was-washed with water, brine, dried over magnesium sulfate, and concentrated under vacuum. Distillation yielded a fraction boiling at 148°–160° C. at 0.1 torr 100 g (0.35 mole) of 1-dimethylcarbamoyl-3-t-butyl-5-carboethoxy-methylthio- 1,2,4-triazole. m.p. 55° C.

METHOD 2:
(a) Preparation of 3-t-butyl-5-thio-1,2,4-1H-triazole

To a suspension of 500 g (5.5 mole) of thiosemicarbazide and 2 liters of tetrahydrofuran (THF) cooled to 10° C. was added over the course of 30 minutes 694 g (5.7 mole) of trimethylacetyl chloride and then 583 g (5.7 mole) of triethylamine. The mixture is stirred at room temperature for 1 hour and heated to reflux for 1 hour and then 1600 ml of THF is removed by distillation. Then 1.5 liters of water and 922 g (11.5 mole) of 50% aqueous sodium hydroxide are added and distillation of the THF/triethylamine is continued until the reaction temperature reaches 80° C. The reaction mixture is refluxed for an additional 3 hours and then cooled to room temperature. The reaction mixture is washed with 1 liter of ethyl acetate which is then discarded. Then 4 kgs of ice and 1 liter of concentrated aqueous hydrochloric acid are added whereon a white solid precipitates. Filtration of the solid and washing with hexane, water, and hexane followed by drying in air affords 746 g of 3-t-butyl-5-thio- 1,2,4-1H-triazole as a white solid, mp 195°–198° C.

(b) Preparation of 3-t-butyl-5-carboethoxymethylthio-1,2,4-1H-triazole

To a solution of 850 g (5.44 mole) of 3-t-butyl-5-thio-1,2,4-1H-triazole and 2 liters of ethyl acetate was added 908 g (5.44 mole) of ethyl bromoacetate maintaining the internal temperature at about 50° C. To this mixture is then added 550 g (5.44 mole) of triethylamine and the mixture is allowed to reflux. The mixture is stirred for an additional 4 hours during which time the temperature slowly returns to room temperature. The mixture is washed with 4 liters of water and the water layer is separated and backwashed with 1 liter of ethyl ether before discarding. The combined organic layers are washed with 2 liters of brine, dried over magnesium sulfate, and concentrated under vaccum. The product is recrystallized from 1 liter of hot hexanes to give 1060 g of 3-t-butyl-5-carboethoxymethylthio- 1,2,4-1H-triazole, mp 94°–95° C.

(c) Preparation of 1-dimethylcarbamoyl-3-t-butyl-5-carboethoxyethylthio- 1,2,4-1H-triazole To a solution of 813 g (3.34 mole) of 3-t-butyl-5-carboethoxymethylthio- 1,2,4-1H-triazole in 2 liters of THF was added 395 g (3.67 mole) of dimethyl carbamoyl chloride and 50 g (0.4 mole) of 4-dimethylaminopyridine. To this solution is slowly added 675 g (6.68 mole) of triethylamine, whereon the reaction exotherms to reflux. The reaction is allowed to react for an additional 1.5 hours whereon the temperature slowly returns to room temperature. One liter of ethyl ether, 2 liters of water, 2 kgs of ice are added and the mixture is acidified with concentrated aqueous hydrochloric acid. The aqueous layer is separated and backwashed with 1 liter of ethyl ether before discarding. The combined aqueous layers are washed with 2 liters of brine, dried over magnesium sulfate, and concentrated under vacuum to afford 1016 g of 1-dimethylcarbamoyl- 3-t-butyl-5-carboethoxymethylthio-1,2,4-1H-triazole as a tan solid.

EXAMPLE NO. 4

Preparation of 1-dimethylcarbamoyl-3-t-butyl-5-(1-carboethoxyethylthio)-1H-1,2,4-triazole By substituting Ethyl 2-bromopropionate for Ethyl bromoacetate in Example 2, step (b) and by following substantially the same procedures described for Example 2, there is obtained 1-dimethylcarbamoyl-3-t-butyl-5-(1-carboethoxyethyl-thio)- 1H-1,2,4-triazole as an oil.

EXAMPLE NO. 6

Preparation of 1-dimethylcarbamoyl-3-t-butyl-5-(3-carboethoxypropylthio)-1H-1,2,4-triazole By substituting Ethyl 4-bromobutyrate for Ethyl bromoacetate in Example 2, step (b) and by following substantially the same procedures described for Example 2, there is obtained 1-dimethylcarbamoyl-3-t-butyl-5-(3-carboethoxypropylthio)- 1H-1,2,4-triazole as an oil.

EXAMPLE NO. 7

Preparation of 1-dimethylcarbamoyl-3-t-butyl-5-
(2-carbomethoxyethylthio) -1H-1,2,4-triazole By substituting methyl 3-bromopropionate for Ethyl bromoacetate in Example 2, step (b) and by following substantially the same procedures described for Example 2, there is obtained 1-dimethylcarbomoyl-3-t-butyl-5-(2-carbomethoxyethylthio)-1H-1,2,4-triazole as an oil.

EXAMPLE NO. 10

Preparation of
1-dimethylcarbamoyl-3-t-butyl-5-carboxymethylthio-1
H-1,2,4-triazole To 1.2 g of 1-dimethylcarbamoyl-3-t-butyl-5-carboethoxymethylthio- 1H-1,2,4-triazole (the compound of Example 2) in 20 ml of THF was added 4 ml of 12M HCl. After stirring for 48 h at 200° C. the reaction mixture was partitioned between ether and water, the ether layer was extracted with dilute NaOH and the resulting aqueous layer was acidified and extracted with fresh ether. The resulting ether layer was dried over magnesium sulfate, filtered and evaporated under vacuum to yield 1-dimethylcarbamoyl-3t-butyl-5-carboxymethylthio-1H-1,2,4-triazole as an oil.

EXAMPLE NO. 20

Preparation of 1-dimethylcarbamoyl-3-t-butyl-5-(N-methylcarboxamidomethylthio)- 1H -1,2,4 -triazole To 3 g (10 mmole) of 1-dimethylcarbamoyl-3-t-butyl-5-carboxymethylthio- 1H-1,2,4-triazole (Example 10) in 15 ml of methylene chloride was added 2.2 ml (15 mmole) of triethylamine. The mixture was cooled to −30° C. and 1.6 ml (11 mmole) of trifluoroacetic anhydride was added. After stirring for 30 minutes at −30° C., 1 g (32 mmole) of monomethylamine was added and the mixture was allowed to warm to room temperature over 30 minutes. The mixture was washed twice with water, dried over magnesium sulfate, concentrated under vaccum and chromatographed on silica gel (ethyl ether) to afford 2.5 g of 1-dimethylcarbamoyl-3-t-butyl-5-(N-methylcarboxamidomethylthio)-1H-1,2,4-triazole, an oil.

EXAMPLE NO. 24

Preparation of
1-dimethylcarbamoyl-3-butyl-5-(N-methyl-
N-phenylcarboxamidoethylthio)- 1H-1,2,4-triazole 3 g (10 mmole) of 1-dimethylcarbamoyl-3-t-butyl-5-carboxymethylthio- 1H-1,2,4-triazole (Example 10 ) was converted to 1-dimethylcarbamoyl-3-t-butyl-5-(N-methyl-N-phenylcarboxamidomethylthio)- 1H-1,2,4-triazole by substantially following the procedure of Example 20 substituting N-methylaniline for monomethylamine. m.p. 119°–120° C.

EXAMPLE NO. 25

Preparation of 1-dimethylcarbamoyl-3-t-butyl-5-
(methylsulfonylmethylthio)-1H-1,2,4-triazole a) Preparation of 3-t-butyl-5-(methylsulfonylmethylthio)-1H-1,2,4-triazole 6.1 g (39 mmole) of 3-t-butyl-5-thio-1H-1,2,4-triazole was dissolved in 25 ml of dimethylformamide (DMF). 4.36 g (39 mmole) of potassium t-butoxide was added and stirred for 5 minutes. 5 g (39 mmole) of chloromethyl methyl sulfone was added and the resulting mixture was refluxed for 4 hours. After cooling, the DMF was evaporated under vaccum and the residue was partitioned between ether and water and dried over magnesium sulfate. Evaporation of the solvent gave 2.7 g of 3-t-butyl-5-(methylsulfonylmethylthio)-1H-1,2,4-triazole, an oil.

b) 2 g (8.0 mmole) of 3-t-butyl-5-(methylsulfonylmethylthio)- 1H-1,2,4-triazole, 0.8 ml (8.8 mmole) of dimethylcarbamoyl chloride, 1.25 ml (9.0 mmole) of triethylamine and 0.1 g (0.8 mmole) of 4-dimethylaminopyridine were dissolved in 20 ml of tetrahydrofuran and refluxed for 4 hours. After removal of the solvent the mixture was partitioned between ether and water, dried over magnesium sulfate and concentrated under vaccum. After chromatography on silica gel, trituration with ether afforded 1.4 g of 1-dimethylcarbamoyl-3-t-butyl-5-(methylsulfonylmethylthio)- 1H-1,2,4-triazole. m.p. 109°–110° C.

EXAMPLE NO. 30

Preparation of
1-dimethylcarbamoyl-3-t-butyl-5-(N-ethyl-
N-methylcarboxamidomethylthio)-1H-1,2,4-triazole 5 g (17 mmole) of 1-dimethylcarbamoyl-3-t-butyl-5-carboxymethylthio- 1H-1,2,4-triazole (Example 10) was converted to 1-dimethylcarbamoyl-3-t-butyl-5-(N-ethyl-N-methylcarboxamidomethylthio)- 1H-1,2,4-triazole by substantially following the procedure of Example 20 substituting methylethylamine for monomethylamine. Yield 2.5 g of an oil.

EXAMPLE NO. 32

Preparation of 1-dimethylcarbamoyl-3-t-butyl-5-
(2-carbomethoxypropyl)-1H-1,2,4-triazole 2 g (13 mmole) of 3-t-butyl-5-thio-1H-1,2,4-triazole was dissolved in 10 ml of acetonitrile. 2.5 ml (14 mmole) of diisopropylethylamine and 2.3 g (13 mmole) of methyl 3-bromo-2-methylpropionate were added. After stirring at 25° C. for 48 hours the solvent was evaporated and the products were partitioned between ether and water. After drying the organic layer with magnesium sulfate, the solvent was evaporated yielding 3-t-butyl-5-(2-carbomethoxypropylthio)- 1H-1,2,4-triazole, an oil.

4.4 g (17 mmole) of 3-t-butyl-5-(2-carbomethoxypropylthio)- 1H-1,2,4-triazole was reacted by substantially following the procedure given in Example 25(b) to afford 2.1 g of 1-dimethylcarbamoyl-3-t-butyl-5-(2-carbomethoxypropylthio)- 1H-1,2,4-triazole, an oil.

EXAMPLE NO. 34

Preparation of 1-dimethylcarbamoyl-3-t-amyl-5-
(carboethoxymethylthio)-1H-1,2,4-triazole a) 9.7 g (106 mmole) of thiosemicarbazide was suspended in 50 ml of tetrahydrofuran (THF) and cooled in an ice bath to 10° C. 15 g (111 mmole) of 2,2-dimethylbutyryl chloride was added while concurrently adding 9.4 g (117 mmole) of 50% aqueous NaOH. The internal temperature was kept below 30° C. After the addition was complete, the mixture was stirred for 30 minutes. Then 16.1 g (201 mmole) of 50% aqueous NaOH and 30 ml of water were added and the mixture was refluxed for 3 hours. After cooling, the mixture was acidified with concentrated hydrochloric acid and extracted with ethyl acetate. The combined organic layers were washed with brine and dried over magnesium sulfate. Evaporation of the solvent gave 18 g of 3-t-amyl-5-thio-1H-1,2,4-triazole, an oil.

b) 9.0 g (52 mmole) of 3-t-amyl-5-thio-1H-1,2,4-triazole, 5.8 ml (52 mmole) of ethyl bromoacetate, and 7.5 ml (54 mmole) of triethylamine were dissolved in 50 ml of ethyl acetate and refluxed for 5 hours. The reaction mixture was washed with water and brine and then dried over magnesium sulfate. After concentration and chromatography on silica gel (ether/hexane), 3-t-amyl-5-(carboethoxymethylthio)-1H-1,2,4-triazole, an oil, is afforded.

c) 5 g (19 mmole) of 3-t-amyl-5-(carboethoxymethylthio)- 1H-1,2,4-triazole was reacted by substantially following the procedure given in Example 25(b) to afford 3.5 g of 1-dimethylcarbamoyl-3-t-amyl-5-(carboethoxymethylthio)-1H-1,2,4-triazole, an oil.

EXAMPLE NO. 35

Preparation of
1-dimethylcarbamoyl-3-(2-methylthio-2-propyl)-5-(carboethoxymethylthio)-1H-1,2,4-triazole a) 60 ml (435 mmole) of diisopropylamine was dissolved in 500 ml of tetrahydrofuran under a nitrogen atmosphere and cooled to −30° C., 160 ml (400 mmole) of 2.5M n-butyllithium in hexanes was added, The reaction mixture was cooled to −70° C. and 46 ml (400 mmole) of methyl isobutyrate was added to this solution over 10 minutes. After stirring for 30 minutes, 36 ml of methyldisulfide was added and the reaction was allowed to warm to 0° C. over 40 minutes. 35 g (545 mmole) of 50% aqueous NaOH and 60 ml of water were added and the mixture was stirred for 18 hrs. The hexane/THF was evaporated and the mixture was then acidified with 12M HCL and extracted with ether taking care to trap the released methyl mercaptan. Distillation afforded 35 g of 2-methylthio-2-methylpropionic acid. b.p. 100°–110° C. at 10 torr.

b) 20 g of 2-methylthio-2-methylpropionic acid, 12 ml of thionyl chloride and 0.2 g of dimethylformamide were heated at 60° C. for 5 hours and then distilled affording 2-methylthio-2-methylpropionyl chloride. b.p. 145°–165 ° C. at 760 torr.

c) 2-methylthio-2-methylpropionyl chloride was reacted, by substantially following the procedure of Example 34(a) to afford 3-(2-methylthio-2-propyl)-5-thio-1H-1,2,4-triazole, an oil.

d) 3-(2-methylthio-2-propyl)-5-thio-1H-1,2,4-triazole was reacted, by substantially following the procedure of Example 34(b) to afford 3-(2-methylthio-2-propyl)5-(carboethoxymethylthio)- 1H-1,2,4-triazole, an oil.

e) 3-(2-methylthio-2-propyl)-5-(carboethoxymethylthio)- 1H-1,2,4-triazole was reacted by substantially following the procedure of Example 34(c) to afford 1-dimethylcarbamoyl-3-(2-methylthio-2-propyl)-5-(carboethoxymethylthio)- 1H-1,2,4-triazole, an oil.

EXAMPLE NO. 40

Preparation of 1-dimethylcarbamoyl-3-t-butyl-5-(dimethylsufonamidomethylthio)-1H-1,2,4-triazole a) 126 g (1.0 mole) sodium sulfite, 500 ml of water, and 186 g (1.0 mole) of dibromomethane were refluxed with vigorous stirring for 3 days, whereon, one layer was observed. Concentration and recrystalization from the water afforded 186 g of bromomethanesulfonic acid sodium salt, mp 285°–300° C.

b) 90 g (0.46 mole) of bromomethanesulfonic acid sodium salt, 96 g (0.46 mole) of phosphorous pentachloride, and 30 ml of phosphorous oxychloride were mixed at 0° C. and then heated in a water bath to 100° C. for 3 hours. After cooling, the mixture was poured onto 300 g of ice. Additional ice was added to maintain the internal temperature below 30° C. After 15 minutes of stirring the mixture was extracted with methylene chloride and the organic layer was dried over magnesium sulfate, concentrated and distilled under vacuum to afford 56 g of bromomethanesulfonyl chloride b.p. 95–105 (1 torr).

c) 20 g (0.1 mole) of bromomethanesulfonyl chloride was dissolved in 100 ml of ethyl ether cooled to 0° C. and 10 g (0.22 mole) of dimethylamine was added. After stirring for 15 minutes the reaction was filtered and the solid was stirred with acetone to separate the product from dimethylamine hydrochloride. Evaporation of the acetone afforded 15 g of N,N-dimethyl bromomethanesulfonamide mp 88°–90° C.

d) 3-t-butyl-5-thio-1H-1,2,4-triazole was reacted with N,N-dimethyl bromomethanesulfonamide by substantially following the procedure of Example 25(a) to afford 3-t-butyl- 5-(dimethylsulfonamidomethylthio)-1H-1,2,4-triazole.

e) 3-t-butyl-5-(dimethylsulfonamidomethylthio)-1H-1,2, 4-triazole was reacted with dimethylcarbamoyl chloride by substantially following the procedure of Example 25(b) to afford 1-dimethylcarbamoyl-3-t-butyl-5-(dimethylsulfonamidomethylthio)- 1H-1,2,4-triazole, mp 83°– 85° C.

By following substantially the procedures for preparing the compounds of the present invention as described above and exemplified by Examples 2, 4, 6, 7, 10, 20, 24, 25, 30, 32, 34, 35 and 40, the compounds of Formula I are prepared.

Surprisingly, many of the compounds of the present invention exhibit better selective aphicidal activity than the closest known compounds. Selectivity of these compounds along with flexibility of application (i.e. to foliage or soil) allows for plant protection without substantial adverse consequences toward beneficial insects and acarids making these compounds especially useful in integrated pest management programs. Accordingly, compounds of the present invention represent a genuine enrichment of the art.

As can be seen by the biological evaluation data, certain of the 1-dimethylcarbamoyl-3-substituted-5-substituted-1H-1,2,4-triazoles of the present invention show, for example, activity at a concentration of from about 0.5 ppm to about 10 ppm against green peach aphids. On the basis of their strong initial aphicidal activity and excellent residual aphicidal activity, compounds according to the invention may be used in low dosages in controlling these pests.

In general, for the control of insects and acarids in agriculture, horticulture and forestry, the compounds of the present invention may be used at a dosage corresponding to from about 10 grams to about 5000 grams of the active substance per hectare and from about 50 grams to about 2500 grams per hectare of the active substance is preferred. The exact amount of dosage for a given situation can be routinely determined and depends on a variety of factors, for example, the substance used, the kind of insect or acarid, the formulation used, the state of the crop infested with the insect or acarid and the prevailing weather conditions. The term "insecticidal" as employed in the specification and claims of this application is to be construed as any means which adversely affects the existence or growth of the target insects. The term "acaricidal" as employed in the specification and claims of this application is to be construed as any means which adversely affects the existence or growth of the target acarid. Such means referring to the terms "insecticidal" and "acaricidal," can comprise a complete killing action, eradication, arresting in growth, inhibition, reducing in number or any combination thereof and includes all measures which adversely affect such pests or protect a plant, crop area or other locus from attack by such pests. "Pesticidal" as employed in the specification and claims of this application is to be construed as insecticidal, acaricidal and/or molluscicidal. The term "control" as employed in the specification and claims of this application is to be construed as meaning pesticidal. By "insecticidally effective amount" or "acaricidally effective amount" is meant that dosage of active substance sufficient to exert insect or acarid "control."

The compounds of the present invention, for practical applications, can be utilized in the form of compositions or formulations. Examples of the preparation of compositions and formulations can be found in the American Chemical Society publication "Pesticidal Formulation Research," (1969) Advances in Chemistry Series No 86, written by Wade Van Valkenburg; and the Marcel Dekker, Inc. publication "Pesticide Formulations," (1973), edited, by Wade Van Valkenburg. In these compositions and formulations, the active substance or substances are mixed with conventional inert (i.e., plant compatible and/or pesticidally inert) diluents or extenders such as solid carrier material or liquid carrier material, of the type usable in conventional compositions or formulations. By agronomically acceptable carrier is meant any substance which can be used to dissolve, disperse or diffuse the active ingredient in the composition without impairing the active ingredient's effectiveness and which by itself has no significant detrimental effect on the soil, equipment, desirable plants or agronomic environment. If desired, conventional adjuvants such as surfactants, stabilizers, antifoam agents and antidrift agents may also be added.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles.

Wettable powders, pastes, flowables and emulsifiable concentrates are concentrated preparations which are diluted with water before or during use.

Baits are preparations generally comprising a food or other substance attractive to the target pest, that includes at least one lethal or non-lethal toxicant. Lethal toxicants kill the pest upon ingesting the bait while non-lethal toxicants change the behavior and physiology of the pest for the purpose of control.

The invert emulsions are mainly used for air application, where large areas are treated with a comparatively small amount of preparation. The invert emulsion may be prepared in the spraying apparatus shortly before, or even during, the spraying operation by emulsifying water in an oil solution or an oil dispersion of the active substance.

Compositions and formulations are prepared in a known manner, for instance by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g., dichlorodifluoromethane and trifluorochloromethane, as well as butane, propane, nitrogen and carbon dioxide; inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g., chlorobenzenes, etc.), cycloalkanes, (e.g., cyclohexane, etc.), paraffins (e.g., petroleum or mineral oil fractions), chlorinated aliphatic hydrocarbons (e.g., methylene chloride, chloroethylenes, etc.), vegetable oils (e.g., soybean oil, cotton seed oil, corn oil, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyctohexanone, isophorone, etc.), and/or water; solid carriers including ground natural minerals, such as kaolins, clays, talc, chalk, quartz, attapulgite, montmorillonite or diatomaceous earth, and ground synthetic minerals, such as highly-dispersed silicic acid, alumina and silicates; solid carriers for granules include crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. The following may be chiefly considered for use as conventional carrier vehicle assistants: emulsifying agents, such as cationic and/or non-ionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

If desired, it is possible to use colorants in compositions and formulations containing compounds of the present invention such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The active compounds of the present invention may be employed alone or in the form of mixtures with one another and/or with such solid and/or liquid dispersible carrier vehicles and/or with other known compatible active agents, especially plant protection agents, such as other acaricides, insecticides, arthropodicides, nematicides, fungicides, bactericides, rodenticides, herbicides, fertilizers, growth-regulating agents, synergists, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1% and 99% by weight, and preferably between about 1% and 75% by weight, of the mixture. Carrier composition mixtures suitable for direct application or field application generally contemplate those in which the active compound is present in an amount substantially between about 0.0001% and 5%, preferably between about 0.001% and 3%, by weight of the mixture. Thus the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, (e.g., a surface-active agent, such as an emulsifying agent and/or a dispersing agent), and an amount of the active compound generally between about 0.0001 and about 99% by weight of the composition, preferably between about 0.001% and about 90% by weight of the composition, and more preferably between about 0.01% and about 75% by weight of the composition which is effective for the purpose in question.

The active compounds can be applied as sprays by methods commonly employed, such as conventional high-gallonage hydraulic sprays, low gallonage sprays, ultra-low-volume sprays, airblast spray, aerial sprays, and dusts. If low volume applications are desired, a solution of the compound is usually used. In ultra-low-volume applications, a liquid composition containing the active compound is usually applied as a spray (e.g., mist) by means of atomizing equipment in finely divided form (average particle size of from about 50 to about 100 microns or less) using airplane crop spraying techniques. Typically only a few liters per hectare are needed and often amounts up to about 15 to 1000 g/hectare, preferbly about 40 to 600 g/hectare are sufficient. With ultra-low-volume, it is possible to use highly concentrated liquid compositions with said liquid carrier vehicles containing from about 20 to about 95% by weight of the active compound.

Furthermore, the present invention contemplates methods of killing, combating or controlling insects, and acarids which comprise contacting insects or acarids with a correspondingly combative or toxic amount (i.e., an insecticidally effective amount or an acaricidally effective amount) of at least one active compound of the invention alone or together with a carrier vehicle (composition or formulation) as noted above. The term "contacting" as employed in the specification and claims of this application is to be construed as applying to at least one of (a) such pests and acarids and (b) the corresponding habitat thereof (i.e., the locus to be protected, for example, to a growing crop or to an area where a crop is to be grown) the active compound of this invention alone or as a constituent of a composition or formulation. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting and the like.

It will be realized, of course, that the concentration of the particular active compound utilized in admixture with the carrier vehicle will depend upon such factors as the type of equipment employed, method of application, area to be treated, types of pests to be controlled and degree of infestation. Therefore, in special cases it is possible to go above or below the aforementioned concentration ranges.

Granular preparations are produced for example, by taking up the active substance in a solvent and by using the resulting solution, as the case may be in the presence of a binder, to impregnate a granular carrier material, such as porous granules (for example pumice and attaclay), or chopped tobacco stems or the like.

A granular preparation (frequently termed a "pellet") may alternatively be produced by compressing the active substance together with powdered minerals in the presence of lubricants and binders and by disintegrating and straining the composite to the desired grain size.

Dusts are obtainable by intimately mixing the active substance with an inert solid carrier material in a concentration of from about 1 to about 50% by weight. Examples of suitable solid carrier materials are talc, kaolin, pipe clay, diatomaceous earth, dolomite, gypsum, chalk, bentonite, attapulgite and colloidal $SiO_2$ or mixtures of these and simular substances. Alternatively organic carrier materials such, for example, as ground walnut shells may be used.

Wettable powders and flowables are produced by mixing from about 10 to about 99 parts by weight of a solid inert carrier such, for example, as the aforementioned carrier materials with from about 1 to about 80 parts by weight of the active substance, from about 1 to about 5 parts by weight of a dispersing agent such as the lignosulfonates or alkyl-naphthalene sulfonates known for this purpose and preferably also from about 0.5 to about 5 parts by weight of a wetting agent, such as fatty alcohol sulfates, or alkylaryl-sulfonates of fatty acid condensation products.

To produce emulsifiable concentrates the active compound is dissolved or finely divided in a suitable solvent which preferably is poorly miscible with water, an emulsifier being added to the resulting solution. Examples of suitable solvents are xylene, toluene, high-boiling aromatic petroleum distillates, for example solvent naphtha, distilled tar oil and mixtures of these liquids. Examples of suitable emulsifiers are alkylphenoxypolyglycol ethers, polyoxyethylene sorbitan esters of fatty acids or polyoxyethylene sorbitol esters of fatty acids. The concentration of the active compound in these emulsifiable concentrates is not restricted within narrow limits and may vary between about 2% and about 50% by weight. A suitable liquid highly concentrated primary composition other than an emulsifiable concentrate is a solution of the active substance in a liquid which is readily miscible with water, for example, acetone, to which solution a dispersent and, as the case may be, a wetting agent are added. When such a primary composition is diluted with water shortly before or during the spraying operation an aqueous dispersion of the active substance is obtained.

An aerosol preparation according to the invention is obtained in the usual manner by incorporating the active substance or a solution thereof in a suitable solvent in a volatile liquid suitable for use as a propellant such, for example, as a mixture of chlorine and fluorine derivatives of methane and ethane.

Fumigating candles or fumigating powders, i.e. preparations which when burning are capable of emitting a pesticidal smoke, are obtained by taking up the active substance in a combustible mixture which may, for example, comprise a sugar or a wood, preferably in the ground form, as a fuel, a substance to sustain combustion such, for example, as ammonium nitrate or potassium chlorate, and furthermore a substance for retarding combustion, for example kaolin, bentonite and/or colloidal silicic acid.

A bait preparation comprises a food or other substance attractive to pests, a carrier, the toxicant and may optionally include other substances commonly used in preparations of this kind, such as, a preservative to inhibit bacterial and fungal growth, a waterproofing agent to prevent disintegration under wet conditions and dyes or colorants as described above.

In addition to the aforementioned ingredients the preparations according to the invention may also contain other substances commonly used in preparations of this kind.

For example, a lubricant, such as calcium stearate or magnesium stearate, may be added to a wettable powder or to a mixture to be granulated. Furthermore there may, for example, be added "adhesives" such as polyvinylalcohol-cellulose derivatives or other colloidal materials, such as casein, to improve the adherence of the pesticide to the surface to be protected.

Representative preparation of compositions and formulations including the compounds of the present invention are set forth below as Examples A through I by way of illustration but not limitation. It should be understood that when compositions and formulations are prepared for use as a plant growth regulator, "toxicant" refers to the active ingredient.

Example A

Granular

| Ingredient | %/wt. |
|---|---|
| Toxicant and toxicant impurities | 0.25 |
| Triton ® X-305 (binder) (Octylphenyl-30-ethylene oxide ethanol) | 0.25 |
| Agsorb ® 24/48 (diluent) (Montmorillonite clay) | 99.50 |

Preparation: The toxicant and Triton® X-305 are dissolved into methylene chloride and the mixture is added to the Agsorb® with continuous mixing. The methylene chloride is then allowed to evaporate.

Example B

Dust

| Ingredient | %/wt. |
|---|---|
| Toxicant and toxicant impurities | 1.0 |
| Talc | 99.0 |

Preparation: Toxicant is dissolved in excess acetone and the mixture is impregnated onto the talc. The acetone is then permitted to evaporate.

Example C

Wettable Powder

| Ingredient | %/wt. |
|---|---|
| Toxicant and toxicant impurities | 31.0 |
| Duponal ® WA Dry (wetter) (Sodium lauryl sulfate) | 2.0 |
| Reax ® 45A (dispersant) (Sodium lignin sulfonate) | 5.0 |
| Barden clay (diluent) | 31.7 |
| HiSil ® 233 (diluent) (Sodium silica) | 30.0 |

Preparation: The toxicant, optionally dissolved in a volatile solvent, is absorbed onto the Barden clay and HiSil® carriers. The Duponal® and Reax® are then added and the entire dry mixture blended until homogeneous. The composition is then micronized to a fine particle size.

Example D

Emulsifiable Concentrate

| Ingredient | %/wt. |
|---|---|
| Toxicant and toxicant impurities | 15.0 |
| Sponto ® 232T (emulsifier) (Anionic and nonionic blend of the following surfactants: calcium dodecyl benzene sulfonate; and ethoxylated alkylphenol) | 6.0 |
| Sponto ® 234T (emulsifier) (Anionic and nonionic blend of the following surfactants: calcium dodecyl benzene sulfonate; and ethoxylated alkylphenol) | 4.0 |
| Cyclohexanone (solvent) | 22.5 |
| Tenneco ® 500-100 (solvent) (Aromatic solvent mixture principally comprising xylene, cumene and ethyl benzene having a boiling point range of 290–345° F.) | 52.5 |

Preparation: All ingredients are mixed together with continuous agitation until a homogeneous clear solution is obtained, Example E Aerosol

| Ingredient | %/wt. |
|---|---|
| Toxicant and toxicant impurities | 0.5 |
| Freon 12 | 99.5 |

Preparation: The components are mixed and packaged under pressure in a suitable container equipped with a release spray valve.

Example F

Fumigating Candle or Fumigating Powder Ingredient

| Ingredient | %/wt. |
|---|---|
| Toxicant and toxicant impurities | 1.0 |
| Wood dust | 96.0 |
| Starch | 3.0 |

Preparation: Toxicant, wood dust and starch are blended together and then molded into a candle using a stall amount of water to activate the starch.

Example G

Bait

Method A

| Ingredient | %/wt. |
| --- | --- |
| Toxicant and toxicant impurities | 1.00 |
| Wheat Bran (carrier and attractant) | 89.95 |
| Corn Syrup (attractant) | 7.00 |
| Corn Oil (attractant) | 2.00 |
| Kathon ® 4200 (preservative) (2-n-octyl-4-isothiazolin-3-one) | 0.05 |

Preparation: The corn oil and corn syrup are added to the wheat bran with adequate mixing. The toxicant and Kathon® are premixed with excess acetone and this solution is added to the wheat bran base with continued mixing. The acetone is then permitted to evaporate.

Method B

| Ingredient | %/wt. |
| --- | --- |
| Toxicant and toxicant impurities | 0.06 |
| Granulated Sugar (carrier and attractant) | 99.94 |

Example H

Pellet

Same as Example G, Method A, with this addition: the bait composition is formed into ¼" diameter by ⅜" long pellets using a suitable die and press apparatus.

Example I

Flowable

| Ingredient | %/wt. |
| --- | --- |
| Toxicant and toxicant impurities | 31.3 |
| Duponal ® WA Dry (wetter) (Sodium lauryl sulfate) | 2.0 |
| Reax ® 45A (dispersant) (Sodium lignin sulfonate) | 5.0 |
| HiSil ® 233 (diluent) (Sodium silica) | 30.0 |
| Kelzan ® (thickener) (Xanthan gum) | 0.5 |
| Water | 31.2 |

Preparation: The toxicant is absorbed onto the HiSil® carrier. The Duponal® and Reax® are then added and the entire dry mixture blended until homogeneous. The composition is then micronized to a fine particle size. The resulting powder is suspended in water and the Kelzan® added.

Compositions and formulations according to the present invention my also include known pesticidal compounds. This expands the spectrum of activity of the preparations and my give rise to synergism.

The following known insecticidal, fungicidal and acaricidal compounds are suitable for use in such a combined preparation.

Insecticides such as:

Chlorinated hydrocarbons, for example, 2,2-bis(p-chlorophenyl)- 1,1,1-trichloroethane and hexachloroepoxyoctahydrodimethanonaphthalene;

Carbamates, for example N-methyl-1-naphthylcarbamate;

Dinitrophenols, for example 2-methyl-4,6-dinitrophenol and (2-(2-butyl)-4,6-dinitrophenol-3,3-dimethylacrylate;

Organic phosphorus compounds, such as dimethyl-2-methoxycarbonyl- 1-methylvinyl phosphate, O,O-diethyl-O-p-nitrophenylphosphorus thioate; N-monomethylamide of O,O-dimethyldithiophosphorylacetic acid;

Diphenylsulfides, for example p-chlorobenzyl or p-chlorophenyl sulfide and 2,4,4',5-tetrachloridiphenylsulfide;

Diphenylsulfonates, for example p-chlorophenylbenzenesulfonate;

Methylcarbinols, for example, 4,4-dichloro-1-trichloromethylbenzhydrol;

Quinozaline compounds, such as methylquinoxaline dithiocarbonate;

Amidines such as N'-(4-chloro-O-tolyl) N,N-dimethylformamidine;

Pyrethroids such as Allethrin;

Biologicals such as *Bacillus thuringiensis* preparations;

Organic tin compounds such as tricyclohexyltin hydroxide;

Synergists such as piperonyl butoxide;

Fungicides such as:

Organic mercury compounds, for example phenylmercuryacetate and methylmercurycyanoguanide;

Organic tin compounds, for example triphenyltin hydroxide and triphenyltin acetate;

Alkylenebisdithiocarbamates, for example, zincethylenebisthiocarbamate and manganoethylenebisthiocarbamate; and furthermore 2,4-dinitro-6-(2-octyl-phenylcrotonate), 1-bis(dimethylamino)phosphoryl-3-phenyl-5-amino- 1,2,4-triazole, 6-methylquinoxaline-2,3-dithiocarbonate, 1,4-dithioantraquinone-2,3-dicarbonitrile, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N'-dimethylsulfonyldiamide and tetrachloroisophthalonitrile.

Biological Activity

It has been found by biological evaluation that compounds according to the present invention have insecticidal, acaricidal, plant growth regulatory and/or molluscicidal activity, especially against insects from the order Homoptera and most especially against insects of the family Aphididae. One skilled in the art will know how to determine the activity of a given compound against a given pest and the dosage required to obtain general or selective pesticidal effects. The compounds of the present invention, particularly the compound of Example 2, have demonstrated both upward and downward mobility in plants. This mobility is believed to be unique in compounds of the general class of 1-(N,N-dialkylcarbamoyl)-3(5)-substituted-5(3)-substituted-1,2,4-triazoles.

In evaluating the foliar insecticidal activity of the compounds of this invention, the following test procedures were employed.

A test solution containing 600 parts per million (ppm) was made by dissolving the test compound in a solvent (acetone:methanol, 1:1), adding water to give an acetone:

methanol: water system of 5:5:90 and then a surfactant. A 1:1 mixture of an alkylarylpolyetheralcohol (sold under the trademark Triton® X-155) and a modified phthalic glycerol alkyl resin (sold under the trademark Triton® B-1956) was utilized at the equivalent of 1 ounce per 100 gal. of test solution as a surfactant.

Analogous solutions are made by serially diluting the 600 ppm test solution with water and surfactant to give concentrations of 150, 38, 10, 2.5, 0.6, 0.15, and 0.038 ppm. Not all compounds are tested at each of the several concentrations stated above.

Initial evaluations were made on all of the following pests:

| Code Symbol | Common Name | Latin Name |
| --- | --- | --- |
| SAW | Southern Armyworm | *Spodoptera eridania* |
| MBB | Mexican Bean Beetle | *Epilachna varivestis* |
| GPA | Green Peach Aphid | *Myzus persicae* |
| TSM | Two-Spotted Spider Mite | *Tetranychus urticae* |

For the bean beetle and armyworm tests, individual bean (*Phaseolus limensis* var. Woods' Prolific) leaves are placed on moistened pieces of filter paper in Petri dishes. The leaves are then sprayed with the test solution using a rotating turntable and allowed to dry. The dishes are infested with 10 third instar larvae of Southern armyworm or Mexican bean beetle. The dishes are then covered.

The percent mortality for each test species and spray concentration is determined 48 hours after treatment. Mortalities obtained are plotted on logarithmic probability paper (No. 3228, Codex Book Co., Inc., Norwood, Mass.). The estimated concentration eliciting a 50 percent mortality ($LC_{50}$) is established from the best eye-fitted line to the plotted mortality data. A second observation 96 hours after treatment my be made at the discretion of the experimenter If it Is believed the effect of a test compound my not be complete or moribund insects appear to evidence some signs of recovery. The $LC_{50}$ value is established as stated above.

For the mite and aphid tests, a pad of moistened cotton is placed in a Petri dish half. Upon one position of this pad is placed a bean (*Phaseolus limensis*) leaf section (approximately 0.75×0.75 inch). Approximately 50 adult female mites are then brushed onto this leaf section. Upon another portion of the cotton pad is placed an infested broccoli (*Brassica oleracea italica* var. DiCicco) leaf containing about 20 adult and immature aphids. The dish, now containing both targets, Is then sprayed with the test solution using a rotating turntable. The open dishes are held for 24 hours at which time the percent mortality is determined for each test species and spray concentration. Derivation of $LC_{50}$ values is as noted for Southern armyworm and Mexican bean beetle.

The rotating turntable consists of a fixed, continuously operating spray nozzle under which targets are rotated at a fixed speed and distance. If the target is a Petri dish (such as for the bean beetle, armyworm, mite or aphid), the distance from the nozzle is 15 inches. The nozzle is located 8 inches from the rotating shaft. The targets on individual platforms revolve around the shaft at 1 revolution per 20 seconds but only a brief portion of this time occurs in the spray path. Targets pass only once under the nozzle and then are removed to drying hoods.

The nozzle used is a 1/4 JCO Spraying Systems (Wheaton, Ill.) air atomizing nozzle equipped with a No. 2850 fluid cap and No. 70 air cap. At the 10 psig air pressure used and with liquid siphon feed 0.5 GPH (gallons per hour) are delivered in a round spray pattern with a 21° spray angle. Targets are misted with spray droplets to the point that the droplets coalesce to form a uniform thin film insufficient to drown test organisms.

Systemic activity of the compounds of the present invention was evaluated employing the following test procedures.

Test solutions are prepared as stated above for foliar insecticidal evaluations. A 10 ml portion of 150 ppm test solution is thoroughly mixed with 200 g of standard greenhouse soil mixture affording 7.5 ppm concentration of test compound in the soil. Approximately 4 week old broccoli (*Brassica oleracea italica* var. DiCicco) or tobacco (*Nicotiana tabacum* var. Greider) seedlings are infested with about 50 aphids per seedling and transplanted into 3-inch pots containing the treated soil and allowed to grow. Similarly, 10 ml of a 5 ppm test solution thoroughly mixed with 200 g of soil affords 0.25 ppm concentration of test compound in the soil; 10 ml of a 20 ppm test solution thoroughly mixed with 200 g of soil affords 1 ppm concentration of test compound in the soil; 10 ml of a 60 ppm test solution thoroughly mixed with 200 g of soil affords 3 ppm concentration of test compound in the soil; 10 ml of an 80 ppm test solution thoroughly mixed with 200 g of soil affords 4 ppm concentration of test compound in the soil; and 10 ml of a 180 ppm test solution thoroughly mixed with 200 g of soil affords 9 ppm concentration of test compound in the soil. The percentage kill is then determined on a scale of 0–100 where 0 indicates no activity and 100 indicates total kill.

All treatments are maintained under existing greenhouse conditions.

The results of the foliar insecticidal evaluations are given in Table II. The selectivity of the 5-position acid and ester compounds of this invention towards aphids is apparent from the results in Table II. Table III sets forth the results of a foliar evaluation comparing a known 1,2,4-triazole outside the scope of the present invention with the compound of Example 2 of the present invention. Table IV sets forth the results of a foliar evaluation comparing a known 1,2,4-triazole outside the scope of the present invention with the compound of Example 7 of the present invention. The results of the systemic insecticidal evaluations of the compounds of the present invention are given in Tables V and VI, along with the results of various known 1,2,4-triazoles outside the scope of the present invention for comparison purposes.

TABLE II

| | Foliar Insecticidal Evaluations $LC_{50}$ Values[a] | | | |
| --- | --- | --- | --- | --- |
| Example No. | TSM | GPA | MBB[b] | SAW[b] |
| 1 | >600 | 1.2 | 300 | >600 |
| 2 | >600 | 2.4 | 300 (260) | 600 |
| 3 | >600 | 19 | 2.5 (45) | >600 |
| 4 | >600 | 5 | 300 (192) | >600 |
| 5 | >600 | 5 | 178 (192) | >600 |
| 6 | >600 | 5 | <150 | >600 |
| 7 | >600 | 1.2 | 300 (460) | >600 |
| 8 | >600 | 1.2 | 192 (300) | >600 |
| 9 | >600 | 5 | 75 | >600 |
| 10 | >600 | 1.2 | >600 | >600 |
| 11 | >600 | 5 | <150 | >600 |
| 12 | >600 | 5 | >600 | >600 |
| 13 | >600 | 41 | >600 | >600 |

TABLE II-continued

Foliar Insecticidal Evaluations
$LC_{50}$ Values[a]

| Example No. | TSM | GPA | MBB[b] | SAW[b] |
|---|---|---|---|---|
| 14 | >600 | 300 | >600 | >600 |
| 15 | >600 | >600[c] | >600 | >600 |
| 16 | >600 | 19 | 400 (600) | >600 |
| 17 | 44 | 2.3 | <38[d] | 350 (500) |
| 18 | >600 | 3.0 | <0.6 (0.54) | >600 |
| 19 | 278 | 5.0 | 22.0 (14) | >150 (100) |
| 20 | 500 | 1.92 | 3.3 (3.0) | 300 (420) |
| 21 | >600 | 70.0 | >600 | >600 |
| 22 | >600 | 28.0 | 760 (390) | >600 |
| 23 | >600 | 11.0 | 76 | >600 |
| 24 | >600 | 9.0 | 125 (150) | >600 |
| 25 | >600 | 4.4 | 150 (192) | >600 |
| 26 | >600 | 6.8 | 10 (13) | >600 |
| 27 | 33 | 9.4 | 13 | 600 |
| 28 | >600 | 11 | 192 | >600 |
| 29 | 295 | 4.9 | 76 (50) | >600 |
| 30 | 180 | 0.52 | 20 (11) | 300 (212) |
| 31 | >600 | 3.3 | 12 | >600 |
| 32 | >600 | 3.9 | 460 (260) | >600 |
| 33 | >600 | 70 | >600 | >600 |
| 34 | >600 | 2.6 | 150 | 500 (300) |
| 35 | >600 | 2.6 | 150 | >600 |
| 36 | >600 | 4.0 | 62 (150) | >600 |
| 37 | >600 | 3.3 | 270 (300) | >600 |
| 38 | >600 | 2.25 | >600 | >600 |
| 39 | >600 | <2.5 | 150 | 300 |
| 40 | >600 | 18 | 150 | >600 |
| 41 | >600 | 1.2 | 115 | >600 |
| 42 | >600 | 11 | 192 (162) | >600 |
| 43 | 600 | 11 | 38 (50) | 600 |
| 44 | >600 | 22 | >600 | >600 |

[a]Concentration in parts per million (ppm) which kills 50 percent of the stated pest ($LC_{50}$).
[b]96 hour results given in parentheses ( ) where observed and different from 48 hour results.
[c]Further evaluation gave on $LC_{50}$ of 105 by somewhat different test methods.
[d]Further evaluation gave an $LC_{50}$ value of 20 ppm after 72 hours and 13 ppm after 114 hours by somewhat different test methods.

TABLE III

Foliar Comparative Evaluation

| Compound or Example No. | Rate (ppm) | % Kill at 24 Hours GPA |
|---|---|---|
| Example 2 of this invention | 2.5 | 50 |
|  | 10 | 100 |
|  | 38 | 100 |
| 1-N,N-dimethylcarbamoyl-3-ethoxycarbonylmethyl-mercapto-5-methyl-1,2,4-triazole (U.S. Pat. No. 3,308,131) | 2.5 | 0 |
|  | 10 | 0 |
|  | 38 | 0 |

TABLE IV

Foliar Activity Comparative Evaluation

| Compound or Example No. | Rate (ppm) | % Kill at 24 hours GPA |
|---|---|---|
| Example 7 of this invention | 600 | 100 |
|  | 38 | 100 |
|  | 2.5 | 100 |
| 1-N,N-dimethylcarbamoyl-3-t-butyl-5-methoxyethyl-thio-1,2,4-triazole (European Patent Application No. 0029407) | 600 | 100 |
|  | 38 | 100 |
|  | 2.5 | 13 |

TABLE V

Systemic Insecticidal Evaluations
Green Peach Aphids on Broccoli
(Comparison of Compounds of this Invention
With Those of the Prior Art)

| Example No. or 5-position Substituent | Rate of Active Ingredient in soil (ppm) | % Control at 9 Weeks Broccoli |
|---|---|---|
| Example 2 of this invention | 0.25 | 47 |
|  | 1 | 100 |
|  | 4 | 100 |
|  | 7.5 | 100 |
| Prior Art Compounds 5-position substituents |  |  |
| —$SCH_3$[1] | 1 | 0 |
|  | 4 | 22 |
|  | 7.5 | 50 |
| —$SCH_2CH=CH_2$[2] | 7.5 | 0 |
| —$SCH_2SCH_3$[3] | 7.5 | 0 |
| —$SCH_2CH_2CH_2CH_2CH_3$[4] | 7.5 | 25 |
| —$SCH_2CH_2C_6H_5$[4] | 7.5 | 44 |

[1]U.S. Pat. No. 4,054,664
[2]U.S. Pat. No. 4,160,839
[3]U.S. Pat. No. 4,291,043
[4]U.S. Pat. No. 3,308,131

TABLE VI

Systemic Biological Evaluations
Green Peach Aphids on Tobacco
(Comparison of Compounds of this Invention
With Those of the Prior Art)

| Example No. or 5-position Substituent | Rate of Active Ingredient in Soil (ppm) | % Control at 21 Days Tobacco |
|---|---|---|
| 1 | 1 | 73 |
|  | 3 | 78 |
|  | 9 | 100 |
| 2 | 1 | 93 |
|  | 3 | 100 |
|  | 9 | 100 |
| 4 | 1 | 93 |
|  | 3 | 90 |
|  | 9 | 100 |
| 5 | 1 | 44 |
|  | 3 | 59 |
|  | 9 | 95 |
| 6 | 1 | 11 |
|  | 3 | 54 |
|  | 9 | 66 |
| 7 | 1 | 52 |
|  | 3 | 59 |
|  | 9 | 78 |
| 8 | 1 | 90 |
|  | 3 | 88 |
|  | 9 | 93 |
| 9 | 1 | 37 |
|  | 3 | 57 |
|  | 9 | 88 |
| Prior Art Compounds |  |  |
| —$SCH_3$[1] | 1 | 15 |
|  | 3 | 57 |

TABLE VI-continued

Systemic Biological Evaluations
Green Peach Aphids on Tobacco
(Comparison of Compounds of this Invention
With Those of the Prior Art)

| Example No.<br>or 5-position<br>Substituent | Rate of Active<br>Ingredient<br>in Soil (ppm) | % Control at<br>21 Days<br>Tobacco |
|---|---|---|
|  | 9 | 93 |
| —SCH$_2$CH=CH$_2$[2] | 1 | 0 |
|  | 3 | 0 |
|  | 9 | 0 |
| —SCH$_2$SCH$_3$[3] | 1 | 0 |
|  | 3 | 0 |
|  | 9 | 90 |
| —SCH$_2$CH$_2$CH$_2$CH$_2$CH$_3$[4] | 1 | 0 |
|  | 3 | 53 |
|  | 9 | 88 |
| —SCH(CH$_2$CH$_3$)$_2$[4] | 1 | 0 |
|  | 3 | 0 |
|  | 9 | 0 |

[1] U.S. Pat. No. 4,054,664
[2] U.S. Pat. No. 4,160,839
[3] U.S. Pat. No. 4,291,043
[4] U.S. Pat. No. 3,308,131

The results in Tables II, III, IV, V and VI demonstrate compounds of the present invention are unexpectedly superior to known triazole derivatives in their aphicidal activity Certain of the compounds of the present invention have demonstrated an observable plant growth regulator effect. The observed effect was stunting of plant height, darkening of the hue of foliage, increase in number, size and thickness of leaves, earlier flowering and suckering. The suckering (branching) occurs below the primary leaves and at the point of leaf stem attachments to the main stem. This branching tissue blooms and gives fruit. An increase in root nodulation on soybeans has also been observed. It is believed the plant growth regulator effects observed will provide increased yields.

The plant growth regulator effects of certain compounds of the present invention were evaluated both foliarly and systemically.

Test solutions containing 1200 ppm, 600 ppm and 300 ppm were made as stated above for evaluating foliar insecticidal activity. An emulsifiable concentrate formulation containing 4 pounds of active ingredient per gallon was also tested and was prepared as follows. All percentages are by weight unless otherwise indicated.

| Toxicant (90% active ingredient) | 53.3 |
|---|---|
| Sponto ® 232T (emulsifier) | 5.0 |
| Sponto ® 234T (emulsifier) | 5.0 |
| Tenneco ® T500-100 (solvent) | 36.7 |
|  | 100.0 |

All ingredients are mixed together with continuous agitation until a homogenous solution is obtained. Formulated material is added to water so as to give concentrations of toxicant equivalent to those of the above-described test solutions.

Lima bean (*Phaseolus limensis* var. Woods' Prolific) and soybean (*Glysine max.* var. Williams) seedlings (about two weeks old) In 6-inch pots were sprayed to runoff with the test solutions using a DeVilbiss atomizer at 20 psig. When dry, each treatment is maintained under greenhouse conditions. Plants are watered as needed.

For systemic evaluations, the same plant varieties used for foliar plant growth regulator evaluation are used. The soil in which two-week old seedlings in 6-inch pots are planted is drenched with the test solution or equivalent 600 ppm active ingredient concentration of the formulation. The volume of material added to soil results in a 30 ppm (weight by volume) concentration in the soil. Each treatment is maintained under greenhouse conditions as noted above and watered as needed.

For foliar evaluation, observations were made 3 days, 7 days, 14 days and 21 days after application, then held until harvest (about 10 weeks). The plant growth regulator effects were first observed at about one week.

For systemic evaluation, observations were made 7 days, 14 days and 21 days after application. The plant growth regulator effects were first observed at about three weeks.

The results of the foliar plant growth regulatory evaluations are given below in Table VII. These results are 21 day observations where "+" indicates plant growth regulatory activity and "−" indicates no activity.

TABLE VII

| Example No. | Plant Growth<br>Regulatory Activity |
|---|---|
| 1 | + |
| 2 | + |
| 3 | − |
| 4 | − |
| 5 | − |
| 6 | − |
| 7 | − |
| 8 | + |
| 9 | − |
| 10 | + |
| 11 | − |
| 12 | + |
| 13 | − |
| 14 | − |
| 15 | − |
| 16 | − |
| 17 | − |
| 18 | − |

When used as plant growth regulators, the compounds of the present invention may be applied in any amount which will be sufficient to effect the desired plant response without causing any undesirable or phytotoxic response. Generally, a dosage corresponding to from about 1 kilogram to about 9 kilograms of the active substance per hectare can be used and from about 3 kilograms to about 6 kilograms per hectare of the active substance is preferred. The exact amount of dosage for a given situation can be routinely determined and depends on a variety of factors, for example, the substance use, the kind of plant, the formulation used, the state of the crop and the prevailing weather conditions.

A preferred method of applying a compound of the present invention as a plant growth regulator agent is by foliar application. The compounds of this invention can be used as plant growth regulators either individually or in mixture. For example, they can be used in combination with other plant growth regulators such as auxins, gibberellins, ethylene-releasing agents such as ethephon, pyridones, pyridazinones, cytokinins, maleic hydrazide, succinic acid 2,2-dimethylhydrazide, (2-chloroethyl)trimethylammonium chloride, triiodobenzoic acid, tributyl-2,4-dichlorobenzylphosphonium chloride, polymeric N-vinyl-2-oxazolidinones, tri(dimethylaminoethyl)phosphate and its salts and N-dimethylamino-1,2,3,6-tetrahydrophthalamic acid and its salts and the like.

The compounds of this invention may be applied to the growth medium or to the plants to be treated either by itself or, as is generally done, as a component in a growth regulant composition or formulation which also comprises an agronomically acceptable carrier. By "agronomically acceptable carrier" is meant any substance which can be used to dissolve, disperse or diffuse a compound in the composition without impairing the effectiveness of the compound and which by itself has no significant detrimental effect on the soil, equipment, crops or agronomic environment. Mixtures of the compounds of the invention may also be used in any of these formulations. The compositions of the invention can be either solid or liquid formulations or solutions. These compositions and formulations have previously been described.

Certain of the compounds of the present invention exhibit molluscicidal activity. In evaluating the molluscicidal activity, the following test procedures were employed.

Mature brown garden snails, *Helix aspersa*, were placed into rectangular plastic boxes (32 cm L×25 cm W× 15 cm H) containing 5 cm of moistened artificial soil. Ten snails were introduced into each container. Fiberglass screening, held in place with rubber bands, was used as a container cover to confine the snails.

Test compounds were formulated in a wheat bran based bait at a level of 1% active ingredient. Fifteen grams of loose bait were applied to the soil surface in five equal piles, one in each corner and one in the center.

The snails were offered the test bait for a 5-day period at which time mortality was recorded.

The results of the molluscicidal evaluation are given below in Table VIII.

TABLE VIII

Molluscicidal Evaluation

| Example No. | Bait Toxicant Concentration | Five Day Mortality |
| --- | --- | --- |
| 2 | 1.0% | 100% |
| 4 | 1.0% | 40% |
| 10 | 1.0% | 0 |
| 17 | 1.0% | 100% |
| 18 | 1.0% | 100% |
| 20 | 1.0% | 70% |
| 25 | .1.0% | 60% |
| 34 | 1.0% | 30% |
| 35 | 1.0% | 50% |

In general, for the control of molluscs in agriculture and horticulture, the compounds of the present invention may be used at a dosage corresponding to from about 2 kilograms to about 9 kilograms of the active substance per hectare and from about 3 kilograms to about 6 kilograms per hectare of the active substance is preferred. The exact amount of dosage for a given situation can be routinely determined and depends on a variety of factors, for example, the substance used, the kind of mollusc, the formulation used, the state of the crop infested and the prevailing weather conditions. The term "molluscicidal" as employed in the specification and claims is to be construed as any means which adversely affects the existence or growth of the target mollusc. Such means can comprise a complete killing action, eradication, arresting in growth, inhibition, reducing in number or any combination thereof. By "molluscicidally effective amount" is meant that dosage of active substance sufficient to exert mollusc "control".

The compounds of the present invention, for practical application as a molluscicide, can be utilized in the form of pesticide compositions or formulations previously described. Preferably, for mollusc control, compounds of the present invention are formulated as a bait.

It is to be understood that the present specification and examples are set forth by way of illustration and not limitation and that various modifications and changes may be made without departing from the spirit and scope of the present invention as defined by the appended claims.

We claim:

1. A compound having the formula:

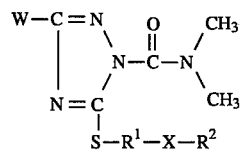

wherein $R^1$ is an unsubstituted or substituted $(C_1-C_6)$ straight chain alkylidene ($-(CH_2)_n-$) group having one to four of the same or different substituents selected from cyano; nitro; OR; $CO_2R$; OCOR; COR; lower $(C_2-C_6)$alkenyl; lower $(C_2-C_6)$alkynyl; lower $(C_1-C_6)$alkyl; or unsubstituted or substituted phenyl having one to three of the same or different halo, cyano, nitro, trifluoromethoxy, difluoromethoxy, tetrafluoroethoxy, trifluorothiomethoxy, tetrafluorothiomethoxy, $CO_2R$, COR, OCOR, lower $(C_1-C_4)$alkyl, lower $(C_1-C_4)$alkoxy, lower $(C_1-C_4)$haloalkyl or lower $(C_2-C_6)$alkenyl;

X is

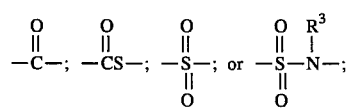

$R^2$ is hydrogen;
unsubstituted or substituted $(C_1-C_6)$alkyl where
the substituent is halo, cyano, nitro, OR, $CO_2R$, COR, or OCOR;
unsubstituted or substituted phen$(C_1-C_4)$alkyl where the phenyl ring has one to three of the same or different substituents selected from halo, cyano, nitro, trifluoromethoxy, difluoromethoxy, tetrafluoroethoxy, trifluorothiomethoxy, tetrafluorothiomethoxy, $CO_2R$, COR, OCOR, lower$(C_1-C_4)$alkyl, lower $(C_1-C_4)$alkoxy, lower $(C_1-C_4)$haloalkyl or lower $(C_2-C_6)$alkenyl;
unsubstituted or substituted phenyl having one to three of the same or different substituents selected from halo, cyano, nitro, trifluoromethoxy, difluoromethoxy, tetrafluoroethoxy, trifluorothiomethoxy, tetrafluorothioethoxy, $CO_2R$, COR, OCOR, lower $(C_1-C_4)$alkyl, lower $(C_1-C_4)$alkoxy, lower $(C_1-C_4)$haloalkyl or lower $(C_2-C_6)$alkenyl;

$R^3$ is hydrogen; or $(C_1-C_6)$alkyl;

$R^2$ and $R^3$ can be taken together along with the nitrogen atom to which they are attached to form a pyrrolidino, morpholino or piperidino ring;

W is isopropyl; sec-butyl; t-butyl; t-amyl; or 2-methylthio-2-propyl;

where R is hydrogen; lower $(C_1-C_6)$alkyl; or phenyl optionally substituted with one to three of the same or different halo, cyano, nitro, hydroxy, trifluoromethyl, trifluoromethoxy, difluoromethoxy, tetrafluoroethoxy, trifluorothiomethoxy, tetrafluorothioethoxy, lower ($C_1$–$C_4$)alkyl, lower ($C_1$–$C_4$)alkoxy, lower ($C_1$–$C_4$)haloalkyl, lower ($C_2$–$C_6$)alkenyl, carboxy, lower ($C_1$–$C_4$)alkoxycarbonyl; and agronomically acceptable salts thereof.

2. A compound according to claim 1 wherein $R^1$ is an unsubstituted or substituted ($C_1$–$C_4$) alkylidene group having one or two substituents selected from lower ($C_1$–$C_4$)alkyl;

X is

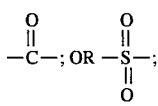

$R^2$ is hydrogen, lower ($C_1$–$C_4$)alkyl, phenyl or benzyl;

$R^3$ is hydrogen or lower ($C_1$–$C_4$)alkyl;

$R^2$ and $R^3$ can be taken together along with the nitrogen atom to which they are attached to form a pyrrolidino, morpholino or piperidino ring;

W is t-butyl; and agronomically acceptable salts thereof.

3. A compound according to claim 2 wherein $R^1$ is —$CH_2$—; —$CH_2CH_2$—; or

X is

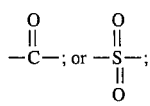

$R^2$ is hydrogen, methyl, ethyl, t-butyl, phenyl or benzyl;

$R^3$ is hydrogen, methyl or ethyl;

$R^2$ and $R^3$ can be taken together along with the nitrogen atom to which they are attached to form a pyrrolidino, morpholino or piperidino ring;

W is t-butyl; and agronomically acceptable salts thereof.

4. A compound according to claim 3 wherein $R^1$ is —$CH_2$—,;

$R^2$ $CH_3$;

$R^3$ is $CH_3$; and

W is t-butyl.

5. A compound according to claim 3 wherein $R^1$ is —$CH_2$—;

$R^2$ is —$CH_2CH_3$;

$R^3$ is —$CH_2CH_3$; and

W is t-butyl.

6. A compound according to claim 3 wherein $R^1$ is —$CH_2$—;

$R^2$ is $CH_3$;

$R^3$ is hydrogen; and

W is t-butyl.

7. A compound according to claim 3 wherein $R^1$ is —$CH_2$—;

X is —$SO_2$—;

$R^2$ is $CH_3$;

W is t-butyl.

8. A compound according to claim 3 wherein $R^1$ is —$CH_2CH_2$—;

$R^2$ is hydrogen;

$R^3$ is hydrogen; and

W is t-butyl.

9. A compound according to claim 3 wherein $R^1$ is —$CH_2CH_2$—;

$R^2$ is $CH_3$;

$R^3$ is $CH_3$; and

W is t-butyl.

10. A compound according to claim 3 wherein $R^1$ is —$CH_2$—;

$R^2$ is —$CH_2CH_3$;

$R^3$ is $CH_3$; and

W is t-butyl.

11. A compound according to claim 3 wherein $R^1$ is —$CH_2$—;

$R^2$is —$CH_2CH_3$;

$R^3$ is hydrogen; and

W is t butyl.

12. A compound according to claim 3 wherein $R^1$ is —$CH_2$—;

X is

$R^2$ is t-butyl; and

W is t-butyl.

13. A compound according to claim 3 wherein $R^1$ is —$CH_2$—;

X is

$R^2$ is hydrogen; and

W is t-butyl.

14. A compound according to claim 3 wherein $R^1$ is —$CH_2$—;

X is

$R^2$ is $CH_3$;

W is t-butyl.

15. A compound according to claim 3 wherein $R^1$ is —$CH_2$—;

$R^2$ and $R^3$ are taken together along with the nitrogen atom to which they are attached to form a pyrrolidino ring;

and

W is t-butyl.

16. A compound according to claim 3 wherein $R^1$ is —$CH_2$—;

$R^2$ and $R^3$ are taken together along with the nitrogen atom to which they are attached to form a piperidino ring; and W is t-butyl.

17. A compound according to claim 3 wherein $R^1$ is —$CH_2$—;

$R^2$ and $R^3$ are taken together along with the nitrogen atom to which they are attached to form a morpholino ring; and W is t-butyl.

18. An insecticidal composition comprising an agronomically acceptable carrier and an insecticidally effective amount of a compound having the formula

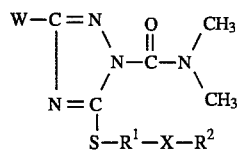

wherein $R^1$ is an unsubstituted or substituted ($C_1$–$C_6$) straight chain alkylidene (—$(CH_2)_n$—) group having one to four of the same or different substituents selected from cyano; nitro; OR; $CO_2R$; OCOR; COR; lower ($C_2$–$C_6$)alkenyl; lower ($C_2$–$C_6$)alkynyl; lower ($C_1$–$C_6$)alkyl; or unsubstituted or substituted phenyl having one to three of the same or different halo, cyano, nitro, trifluoromethoxy, difluoromethoxy, tetrafluoroethoxy, trifluorothiomethoxy, tetrafluorothiomethoxy, $CO_2R$, COR, OCOR, lower ($C_1$–$C_4$)alkyl, lower ($C_1$–$C_4$)alkoxy, lower ($C_1$–$C_4$)haloalkyl or lower ($C_2$–$C_6$)alkenyl;

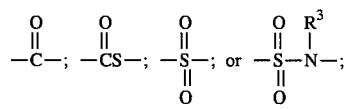

$R^2$ is hydrogen;

unsubstituted or substituted ($C_1$–$C_6$)alkyl where the substituent is halo, cyano, nitro, OR, $CO_2R$, COR, or OCOR;

unsubstituted or substituted phen($C_1$–$C_4$)alkyl where the phenyl ring has one to three of the same or different substituents selected from halo, cyano, nitro, trifluoromethoxy, difluoromethoxy, tetrafluoroethoxy, trifluorothiomethoxy, tetrafluorothiomethoxy, $CO_2R$, COR, OCOR, lower($C_1$–$C_4$)alkyl, lower ($C_1$–$C_4$)alkoxy, lower ($C_1$–$C_4$)haloalkyl or lower ($C_2$–$C_6$)alkenyl;

unsubstituted or substituted phenyl having one to three of the same or different substituents selected from halo, cyano, nitro, trifluoromethoxy, difluoromethoxy, tetrafluoromethoxy, trifluorothiomethoxy, tetrafluorothioethoxy, $CO_2R$, COR, OCOR, lower ($C_1$–$C_4$)alkyl, lower ($C_1$–$C_4$)alkoxy, lower ($C_1$–$C_4$)haloalkyl or lower ($C_2$–$C_6$)alkenyl;

$R^3$ is hydrogen; or ($C_1$–$C_6$)alkyl;

$R^2$ and $R^3$ can be taken together along with the nitrogen atom to which they are attached to form a pyrrolidino, morpholino or piperidino ring;

W is isopropyl; sec-butyl; t-butyl; t-amyl; or 2-methylthio-2-propyl;

where R is hydrogen; lower ($C_1$–$C_6$)alkyl; or phenyl optionally substituted with one to three of the same or different halo, cyano, nitro, hydroxy, trifluoromethyl, trifluoromethoxy, difluoromethoxy, tetrafluoroethoxy, trifluorothiomethoxy, tetrafluorothioethoxy, lower ($C_1$–$C_4$)alkyl, lower ($C_1$–$C_4$)alkoxy, lower ($C_1$–$C_4$)haloalkyl, lower ($C_2$–$C_6$)alkenyl, carboxy, lower ($C_1$–$C_4$)alkoxycarbonyl; and agronomically acceptable salts thereof.

19. The composition according to claim 18 wherein $R^1$ is an unsubstituted or substituted ($C_1$–$C_4$) alkylidene group having one or two substituents selected from lower ($C_1$–$C_4$)alkyl;

X is

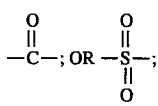

$R^2$ is hydrogen, lower ($C_1$–$C_4$)alkyl, phenyl or benzyl;

$R^3$ is hydrogen or lower ($C_1$–$C_4$)alkyl;

$R^2$ and $R^3$ can be taken together along with the nitrogen atom to which they are attached to form a pyrrolidino, morpholino or piperidino ring;

W is t-butyl; and agronomically acceptable salts thereof.

20. The composition according to claim 19 wherein $R^1$ is —$CH_2$—; —$CH_2CH_2$—; or

X is

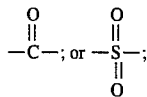

$R^2$ is hydrogen, methyl, ethyl, t-butyl, phenyl or benzyl;

$R^3$ is hydrogen, methyl or ethyl;

$R^2$ and $R^3$ can be taken together along with the nitrogen atom to which they are attached to form a pyrrolidino, morpholino or piperidino ring;

W is t-butyl; and agronomically acceptable salts thereof.

21. The composition according to claim 18 wherein said compound is present at from about 0.0001 to about 99% by weight of the composition.

22. The composition according to claim 19 wherein said compound is present at from about 0.0001 to about 99% by weight of the composition.

23. The composition according to claim 20 wherein said compound is present at from about 0.0001 to about 99% by weight of the composition.

24. The composition according to claim 21 wherein said compound is present at from about 0.001 to about 90% by weight of the composition, 25. The composition according to claim 22 wherein said compound is present at from about 0.001 to about 90% by weight of the composition.

26. The composition according to claim 23 wherein said compound is present at from about 0.001 to about 90% by weight of the composition.

27. The composition according to claim 24 wherein said compound is present at from about 0.01 to about 75% by weight of the composition.

28. The composition according to claim 25 wherein said compound is present at from about 0.01 to about 75% by weight of the composition.

29. The composition according to claim 26 wherein said compound is present at from about 0.01 to about 75% by weight of the composition, 30. The composition according to claim 29 wherein said compound is 1-dimethylcarbamoyl-3-t-butyl-5-(methylsulfonylmethylthio)-1H-1,2,4-triazole.

31. The composition according to claim 29 wherein said compound is 1-dimethylcarbamoyl-3-t-butyl-5-(trimethylacetylmethylthio)-1H-1,2,4-triazole.

32. The composition according to claim 29 wherein said compound is 1-dimethylcarbamoyl-3-t-butyl-5-(formylmethylthio)-1H-1,2,4-triazole.

33. The composition according to claim 29 wherein sad compound is 1-dimethylcarbamoyl-3-t-butyl-5-(acetylmethylthio)-1H-1,2,4-triazole.

34. The insecticidal composition according to claim 29 wherein said agronomically acceptable carrier is a liquid.

35. The insecticidal composition according to claim 34 additionally containing an emulsifying agent, said composition being in the form of an emulsifiable concentrate.

36. The insecticidal composition according to claim 29 wherein said agronomically acceptable carrier is a solid.

37. The insecticidal composition according to claim 36 additionally containing a dispersing agent, said composition being in the form of a wettable powder.

38. The insecticidal composition according to claim 36 additionally containing a liquid agronomically acceptable carrier and a dispersing agent, said composition being in the form of a flowable.

39. The insecticidal composition according to claim 36 wherein said composition is in the form of a dust.

40. The insecticidal composition according to claim 36 additionally containing a binding agent, said composition being in the form of a granule.

41. The insecticidal composition according to claim 36 additionally containing an attractant agent, said composition being in the form of a bait.

42. A method of controlling insects which comprises contacting said insects with an insecticidally effective amount of a compound having the formula $$\begin{array}{c} W-C=N \\ | \quad \backslash \quad O \quad CH_3 \\ | \quad \quad N-C-N \\ | \quad / \quad \quad \backslash \\ N=C \quad \quad CH_3 \\ | \\ S-R^1-X-R^2 \end{array}$$

wherein $R^1$ is an unsubstituted or substituted $(C_1-C_6)$ straight chain alkylidene $(-(CH_2)_n-)$ group having one to four of the same or different substituents selected from cyano; nitro; OR; $CO_2R$; OCOR; COR; lower $(C_2-C_6)$alkenyl; lower $(C_2-C_6)$alkynyl; lower $(C_1-C_6)$alkyl; or unsubstituted or substituted phenyl having one to three of the same or different halo, cyano, nitro, trifluoromethoxy, difluoromethoxy, tetrafluoroethoxy, trifluorothiomethoxy, tetrafluorothiomethoxy, $CO_2R$, COR, OCOR, lower $(C_1-C_4)$alkyl, lower $(C_1-C_4)$alkoxy, lower $(C_1-C_4)$haloalkyl or lower $(C_2C_6)$alkenyl;

X is $$\begin{array}{c} O \quad\quad O \quad\quad O \quad R^3 \quad O \quad\quad O \quad R^3 \\ \| \quad\quad \| \quad\quad \| \quad | \quad\quad \| \quad\quad \| \quad | \\ -C-; -CS-; -C-N-; -S-; \text{ or } -S-N-; \\ \quad\quad\quad\quad\quad\quad\quad\quad\quad\quad \| \quad\quad\quad\quad \| \\ \quad\quad\quad\quad\quad\quad\quad\quad\quad\quad O \quad\quad\quad\quad O \end{array}$$

$R^2$ is hydrogen;
 unsubstituted or substituted $(C_1-C_6)$alkyl where the substituent is halo, cyano, nitro, OR, $CO_2R$, COR, or OCOR;
 unsubstituted or substituted phen$(C_1-C_4)$alkyl where the phenyl ring has one to three of the same or different substituents selected from halo, cyano, nitro, trifluoromethoxy, difluoromethoxy, tetrafluoroethoxy, trifluorothiomethoxy, tetrafluorothiomethoxy $CO_2R$, COR, OCOR, lower$(C_1-C_4)$alkyl, lower $(C_1-C_4)$alkoxy, lower $(C_1-C_4)$haloalkyl or lower $(C_2-C_6)$alkenyl;
 unsubstituted or substituted phenyl having one to three of the same or different substituents selected from halo, cyano, nitro, trifluoromethoxy, difluoromethoxy, tetrafluoroethoxy, trifluorothiomethoxy, tetrafluorothioethoxy, $CO_2R$, COR, OCOR, lower $(C_1-C_4)$alkyl, lower $(C_1-C_4)$alkoxy, lower $(C_1-C_4)$haloalkyl or lower $(C_2-C_6)$alkenyl;

$R^3$ is hydrogen; or $(C_1-C_6)$alkyl;

$R^2$ and $R^3$ can be taken together along with the nitrogen atom to which they are attached to form a 5 or 6-membered pyrrolidino, morpholino or piperidino ring;

W is isopropyl; sec-butyl; t-butyl; t-amyl; or 2-methylthio-2-propyl;

where R is hydrogen; lower $(C_1-C_6)$alkyl; or phenyl optionally substituted with one to three of the same or different halo, cyano, nitro, hydroxy, trifluoromethyl, trifluoromethoxy, difluoromethoxy, tetrafluoroethoxy, trifluorothiomethoxy, tetrafluorothioethoxy, lower $(C_1-C_4)$alkyl, lower $(C_1-C_4)$alkoxy, lower $(C_1-C_4)$haloalkyl, lower $(C_2-C_6)$alkenyl, carboxy, lower $(C_1-C_4)$alkoxycarbonyl; and agronomically acceptable salts thereof.

43. The method of claim 42 wherein
$R^1$ is an unsubstituted or substituted $(C_1-C_4)$ alkylidene group having one or two substituents selected from lower $(C_1-C_4)$alkyl;

X is $$\begin{array}{c} O \quad\quad O \quad R^3 \quad\quad\quad O \\ \| \quad\quad \| \quad | \quad\quad\quad \| \\ -C-; -C-N-; \text{ OR } -S-; \\ \quad\quad\quad\quad\quad\quad\quad\quad\quad \| \\ \quad\quad\quad\quad\quad\quad\quad\quad\quad O \end{array}$$

$R^2$ is hydrogen, lower $(C_1-C_4)$alkyl, phenyl or benzyl;

$R^3$ is hydrogen or lower $(C_1-C_4)$alkyl;

$R^2$ and $R^3$ can be taken together along with the nitrogen atom to which they are attached to form a pyrrolidino, morpholino or piperidino ring;

W is t-butyl; and agronomically acceptable salts thereof.

44. The method of claim 43 wherein $R^1$ is —$CH_2$—; —$CH_2CH_2$—; or $$\begin{array}{c} CH_3 \\ | \\ -CH- \end{array};$$

X is $$\begin{array}{ccc} O & O & R^3 & O \\ \| & \| & | & \| \\ -C-; & -C-N-; \text{ or } & -S-; \\ & & & \| \\ & & & O \end{array}$$

$R^2$ is hydrogen, methyl, ethyl, t-butyl, phenyl or benzyl;

$R^3$ is hydrogen, methyl or ethyl;

$R^2$ and $R^3$ can be taken together along with the nitrogen atom to which they are attached to form a pyrrolidino, morpholino or piperidino ring;

W is t-butyl; and agronomically acceptable salts thereof.

45. A method of controlling insects which comprises contacting said insects with an insecticidally effective amount of a composition according to claim 18.

46. A method of controlling insects which comprises contacting said insects with an insecticidally effective amount of a composition according to claim 19.

47. A method of controlling insects which comprises contacting said insects with an insecticidally effective amount of a composition according to claim 20.

48. The method of claim 42 wherein said compound is applied at from about 10 grams to about 5000 grams per hectare.

49. The method of claim 43 wherein said compound is applied at from about 10 grams to about 5000 grams per hectare.

50. The method of claim 44 wherein said compound is applied at from about 10 grams to about 5000 grams per hectare.

51. The method of claim 42 wherein said compound is applied at from about 50 grams to about 2500 grams per hectare.

52. The method of claim 43 wherein said compound is applied at from about 50 grams to about 2500 grams per hectare.

53. The method of claim 44 wherein said compound is applied at from about 50 grams to about 2500 kilogram perhectare.

54. The method of claim 53 wherein the compound is 1-dimethylcarbamoyl-3-t-butyl-5-(N,N-dimethylcarboxamidomethylthio)- 1H-1,2,4-triazole.

55. The method of claim 53 wherein the compound is 1-dimethylcarbamoyl-3-t-butyl-5-(N,N-diethylcarboxamidomethylthio)-1H-1,2,4-triazole.

56. The method of claim 53 wherein the compound is 1-dimethylcarbamoyl- 3-t-butyl-5-(N-methylcarboxamidomethylthio)-1H-1,2,4-triazole.

57. The method of claim 53 wherein the compound is 1-dimethylcarbamoyl- 3-t-butyl-5-(methylsulfonylmethylthio)-1H-1,2,4-triazole.

58. The method of claim 53 wherein the compound is 1-dimethylcarbamoyl- 3-t-butyl-5-(carboxamidoethylthio)-1H-1,2,4-triazole.

59. The method of claim 53 wherein the compound is 1-dimethylcarbamoyl-3-t-butyl-5-(N,N-dimethylcarboxamidoethylthio)- 1H-1,2,4-triazole.

60. The method of claim 53 wherein the compound is 1-dimethylcarbamoyl-3-tbutyl-5-(N-methyl-N-ethylcarboxamidomethylthio)-1H-1,2,4-triazole.

61. The method of claim 53 wherein the compound is 1-dimethylcarbamoyl- 3-t-butyl-5-(N-ethylcarboxamidomethylthio)- 1H-1,2,4-triazole.

62. The method of claim 53 wherein the compound is 1-dimethylcarbamoyl- 3-t-butyl-5-(trimethylacetylmethylthio) 1H-1,2,4-triazole.

63. The method of claim 53 wherein the compound is 1-dimethylcarbamoyl-3-t-butyl-5-(formylmethylthio)-1H-1,2,4-triazole.

64. The method of claim 53 wherein the compound is 1-dimethylcarbamoyl-3-t-butyl-5-(acetylmethylthio)-1H-1, 2,4-triazole.

65. The method of claim 53 wherein the compound is 1-dimethylcarbamoyl- 3-t-butyl-5-(pyrrolidinocarbonylmethyl)-1H-1,2,4-triazole.

66. The method of claim 53 wherein the compound is 1-dimethylcarbamoyl)-3-t-butyl-5-(piperidinocarbonylmethylthio)-1H-1,2,4-triazole.

67. The method of claim 53 wherein the compound is 1-dimethylcarbamoyl- 3-t-butyl-5-(morpholinocarbonylmethylthio)-1H-1,2,4-triazole.

68. A molluscicidal composition comprising an agronomically acceptable carrier and a molluscicidally effective amount of a compound having the formula $$\begin{array}{c} W-C=N \\ | \quad \quad \backslash \quad O \quad CH_3 \\ \quad \quad \quad N-C-N \\ | \quad \quad / \quad \quad \backslash \\ N=C \quad \quad \quad CH_3 \\ | \\ S-R^1-X-R^2 \end{array}$$

wherein $R^1$ is —$CH_2$— or —$CH(CH_3)$—;

X is —$SO_2$—;

$R^2$ is hydrogen, methyl or ethyl;

W is t-butyl, t-amyl, or 2-methylthio-2-propyl; and agronomically acceptable salts thereof.

69. A composition according to claim 68 wherein $R^1$ is —$CH_2$—;

$R^2$ is hydrogen, methyl or ethyl;

W is t-butyl; and agronomically acceptable salts thereof.

70. A method of controlling molluscs which comprises contacting molluscs with a molluscicidally effective amount of a compound having the formula $$\begin{array}{c} W-C=N \\ | \quad \quad \backslash \quad O \quad CH_3 \\ \quad \quad \quad N-C-N \\ | \quad \quad / \quad \quad \backslash \\ N=C \quad \quad \quad CH_3 \\ | \\ S-R^1-X-R^2 \end{array}$$

wherein $R^1$ is —$CH_2$— or —$CH(CH_2)$—;

X is —$CO_2$—;

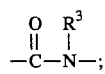

or —SO$_2$—;

R$^2$ is hydrogen, methyl or ethyl;

R$^3$ is hydrogen or lower(C$_1$–C$_4$)alkyl;

W is t-butyl, t-amyl, or 2-methylthio-2-propyl; and agronomically acceptable salts thereof.

71. The method of claim 70 wherein

R$^1$ is —CH$_2$—;

X is —CO$_2$— or

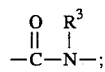

R$^2$ and R$^3$ are, independently, hydrogen, methyl or ethyl;

W is t-butyl; and agronomically acceptable salts thereof.

72. The method of claim 71 wherein said compound is applied at from about 2 kilograms to about 9 kilograms per hectare.

73. The method of claim 72 wherein said compound is applied at from about 3 kilograms to about 6 kilograms per hectare.

74. The method of claim 73 wherein the compound is 1-dimethylcarbamoyl- 3-t-butyl-5-(carboethoxymethylthio)-1H-1,2,4-triazole.

75. The method of claim 73 wherein the compound is 1-dimethylcarbamoyl- 3-t-butyl-5-(N,N-dimethylcarboxamidomethyltho)-1H-1,2,4-triazole.

76. The method of claim 73 wherein the compound is 1-dimethylcarbamoyl-3-t-butyl-5-(carboxamidomethylthio)-1H-1,2,4-triazole.

\* \* \* \* \*

UNITED STATES PATENT AND TRADEMARK OFFICE
CERTIFICATE OF CORRECTION

PATENT NO. : 5,470,984
DATED : November 28, 1995
INVENTOR(S) : RICHARD M. JACOBSON ET AL.

It is certified that error appears in the above-indentified patent and that said Letters Patent is hereby corrected as shown below:

Claim 33, column 43, line 1 of the claim, "sad" should read
--said--.

Claim 53, column 45, line 3 of the claim, "perhectare" should read
--per hectare--.

Claim 60, column 46, line 2 of the claim, "tbutyl" should read
--t-butyl--.

Claim 65, column 46, line 3 of the claim, "ethyl)" should read
--ethylthio)--.

Claim 70, column 46, line 9 of the claim, "$CH(CH_2)$" should read
--$CH(CH_3)$--.

Claim 75, column 48, line 3 of the claim, "midomethyltho" should read
--midomethylthio--.

Signed and Sealed this

Second Day of April, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,470,984

DATED : November 28, 1995

INVENTOR(S) : RICHARD M. JACOBSON ET AL.

It is certified that error appears in the above-indentified patent and that said Letters Patent is hereby corrected as shown below:

Claim 1, column 38, line 34 (now blank), --X is-- should be inserted.

Claim 18, column 41, line 41 (now blank), --X is-- should be inserted.

Signed and Sealed this

Twenty-fifth Day of August, 1998

Attest:

BRUCE LEHMAN

Attesting Officer

Commissioner of Patents and Trademarks